US008133498B2

(12) United States Patent
Fairhead

(10) Patent No.: US 8,133,498 B2
(45) Date of Patent: Mar. 13, 2012

(54) USE OF POLYNUCLEOTIDES ENCODING SMALL ACID-SOLUBLE SPORE PROTEIN FOR INHIBITING BACTERIAL CELL GROWTH AND/OR TREATING BACTERIAL INFECTIONS

(75) Inventor: Heather Marie Fairhead, Histon (GB)

(73) Assignee: Phico Therapeutics Ltd., Babraham (GB)

( * ) Notice: Subject to any disclaimer, the term of this patent is extended or adjusted under 35 U.S.C. 154(b) by 0 days.

(21) Appl. No.: 12/611,604

(22) Filed: Nov. 3, 2009

(65) Prior Publication Data

US 2010/0209393 A1    Aug. 19, 2010

Related U.S. Application Data

(62) Division of application No. 10/416,800, filed as application No. PCT/GB01/05061 on Nov. 16, 2001, now Pat. No. 7,632,512.

(30) Foreign Application Priority Data

Nov. 17, 2000 (GB) .................................. 0028130.3

(51) Int. Cl.
*A61K 39/07* (2006.01)
(52) U.S. Cl. ............... 424/246.1; 435/235.1; 435/252.3; 435/320.1; 536/23.7; 424/234.1; 424/239.1
(58) Field of Classification Search .................... None
See application file for complete search history.

(56) References Cited

U.S. PATENT DOCUMENTS

| 5,766,892 A | 6/1998 | Merril et al. |
| 7,459,272 B2 | 12/2008 | Morris et al. |

FOREIGN PATENT DOCUMENTS

| WO | WO 99/55720 | 11/1999 |
| WO | WO 00/03018 | 1/2000 |

OTHER PUBLICATIONS

Loshon et al (J.Bacteriol. 1986. 167: 168-173).*
Walker et al (Route Maps in Gene Technol, 1997, Chr 70: Delivering DNA into cells, pp. 186-187 http://books.google.com/books?id=FESpp_3ZUkMC&pg=PA186&dq=delivery+system+dna+rna+bacteriophage&hl=en&ei=awS_TdbNKcnTgQfR_MniBg&sa=X&oi=book_result&ct=result&resnum=4&ved=0CGMQ6AEwAw#v=onepage&q=delivery%20system%20dna%20rna%20bacteriophage&f=false).*
Reference viewable at the html cited above.*
Setlow, et al., "Synthesis of a *Bacillus subtilis* small, acid-soluble spore protein in *Escherichia coli* causes cell DNA to assume some characteristics of spore DNA" Journal of Bacteriology, vol. 173, No. 5, Mar. 1991, pp. 1642-1653.

Setlow, et al., "Mutation and killing of *Escherichia coli* expressing a cloned *Bacillus subtilis* gene whose product alters DNA conformation" Journal of Bacteriology, vol. 174, No. 9, May 1992, pp. 2943-2950.
International Search Report.
Bonnie Ann Wallace, et al., "BBS—What is Biophysics?: Circular Dichrosim Spectroscopy".
Christopher S. Hayes, et al., "An alpha/beta-Type, Small, Acid-Soluble Spore Protein Which Has Very High Affinity for DNA Prevents Outgrowth of *Bacillus subtilis* Spores" Journal of Bacteriology, Apr. 2001, pp. 2662-2666.
James M. Mason, at al., "Different Small, Acid-Soluble Proteins of the alpha/beta Type Have Interchangeable Roles in the Heat and UV Radiation Resistance of *Bacillus subtilis* Spores" Journal of Bacteriology, Aug. 1987, pp. 3633-3637.
Scott C. Mohr, et al., "Binding of small acid-soluble spore proteins from *Bacillus subtilis* changes the conformation of DNA from B to A" Proc. Natl. Acad. Of Science, vol. 88, Jan. 1991. pp. 77-81.
Jun Cao, at al., "*Helicobactor pylori*-antigen-binding fragments expressed on the filamentous M13 phage prevent bacterial growth" Biochimica at Biophysica Acta, vol. 1474, 2000, pp. 107-113.
J. E. Donnellen, at al., "Thymine Photoroducts but not Thymine Dimers Found in Ultra-violet-Irradiated Bacterial Spores" Science, vol. 149, pp. 308-310.
Heather Fairhead, et al., "Prevention of DNA Damage in Spores and In Vitro by Small, Acid-Soluble Proteins from *Bacillus subtilis* Species" Journal of Bacteriology, Mar. 1998, pp. 1367-1374.
Heather Fairhead, at al., "Binding of DNA to alpha/beta-Type Small, Acid-Soluble Proteins from Spores of *Bacillus* or *Clostridium* Species Prevents Formation of Cytosine Dimers, Cytosine-Thymine Dimers, and Bipyrimidine Photoadducts after UV Irradiation" Journal of Bacteriology, May 1992, pp. 2874-2880.
Rebecca Hawes Hackett, et al., "Cloning, Nucleotide Sequencing, and Genetic Mapping of the Gene of Small, Acid-Soluble Spore Protein γ of *Bacillus subtilis*" Journal of Bacteriology, May 1987, pp. 1985-1992.
Christopher S. Hayes, at al., "Equilibrium and Kinetic Binding Interactions between DNA and a Group of Novel, Nonspecific DNA-binding Proteins from Spores of *Bacillus* or *Clostridium* Spores" Journal of Biological Chemistry, vol. 275, No. 45, Nov. 10, 2000, pp. 35040-35050.
Paul D. Kassner, at al., "Genetic Selection of Phage Engineered for Receptor-Mediated Gene Transfer to Mammalian Cells" Biochemical and Biophysical Research Communications, vol. 264, 1999, pp. 921-928.
Tobias Kieser, "Factors Affecting the Isolation of CCC DNA from *Steptomyces lividans* and *Escherichia coli*" Plasmid, vol. 12, 1984, pp. 19-36.
Walter Keller, "Determination of the number of superhelical turns in simian virus DNA by gel electrophoresis" Proc. Natl. Acad. Of Science, vol. 72, No. 12, Dec. 1975, pp. 4876-4880.
David LaRocca, et al., "Targeting Bacteriophage to Mammalian Cell Surface Receptors for Gene Delivery" Human Gene Therapy, vol. 9, Nov. 1, 1998, pp. 2393-2399.

(Continued)

Primary Examiner — Jennifer Graser
(74) Attorney, Agent, or Firm — Crowell & Moring LLP

(57) ABSTRACT

A polypeptide having α/β type SASP activity, for use as a medicament.

10 Claims, 13 Drawing Sheets

OTHER PUBLICATIONS

David LaRocca, et al., "Gene transfer to mammalian cells using genetically targeted filamentous bacteriophage" The FASEB Journal, vol. 13, Apr. 1999, pp. 727-734.

Wayne L. Nicholson, et al., "Dramatic Increase in Negative Superhelicity of Plasmid DNA in the Forespore Compartment of Sporulating Cells of *Bacillus subtilis*" Journal of Bacteriology, Jan. 1999, pp. 7-14.

Wayne L. Nicholson, et al., "Binding of DNA In Vitro by a Small, Acid-Soluble Spore Protein from *Bacillus subtilis* and the Effect of This Binding on DNA Topology" Journal of Bacteriology, Dec. 1990, pp. 6900-6906.

Wayne L. Nicholson, et al., "Ultraviolet irradiation of DNA complexed with alpha/beta-type small, acid soluble proteins from spores of *Bacillus* or *Clostridium* species makes spore photoproduct but not thymine dimers" Proc. Natl. Acad. Of Science, vol. 88, Oct. 1991, pp. 8288-8292.

Walter Pohle, et al., "A new conformation-specific infrared band of A-DNA in films" Nucleic Acid Research, vol. 8, No. 11, 1980, pp. 2527-2535.

Marie-Alix Poul, et al., "Targeted Gene Delivery to Mammalian Cells by Filamentous Bacteriophage" J. Mol. Biology, vol. 288, 1999, pp. 203-211.

J. Sambrook, et al., "Molecular Cloning: A Laboratory Manual" 1989.

Barbara Setlow, at al., "Interaction between DNA and alpha/beta-Type Small, Acid Soluble Spore Proteins: a New Class of DNA-binding Protein" Journal of Bacteriology, Apr. 1992, pp. 2312-2322.

Peter Setlow, "Small, Acid-Soluble Spore Proteins of *Bacillus* Species: Structure, Synthesis, Genetics, Function and Degradation" Ann. Rev. Microbiology, vol. 42, 1988,pp. 319-338.

Gert De Vries, at al., "Extension of bacteriophage λ host range: Selection, cloning, and characterization of a constitutive λ receptor gene" Pro. Natl. Acad. Of Science, vol. 81, Oct. 1984, pp. 6080-6084.

Connors, Michael J. at al., "Cloning and Nucleotide Sequencing of Genes for Three Small, Acid-Soluble Proteins from *Bacillus subtills* Spores" Journal of Bacteriology, vol. 166 No. 2, May 1986, pp. 417-425.

Notice of Reasons for Refusal dated May 29, 2007 with an English translation (Six (6) pages).

Fliss, E.R.; Setlow, P.L.J. Bacteriol. 158, 809-813, 1984.

Setlow, P.; Gerard, C.; Ozols, J. Biol. Chem. 255, 3624-3828, 1980.

Setlow, P.; Ozols, J. J. Biol. Chem. 255, 8413-8416, 1980.

* cited by examiner

USE OF POLYNUCLEOTIDES ENCODING SMALL ACID-SOLUBLE SPORE PROTEIN FOR INHIBITING BACTERIAL CELL GROWTH AND/OR TREATING BACTERIAL INFECTIONS

CROSS REFERENCE TO RELATED APPLICATIONS

This application is a division of application Ser. No. 10/416,800, filed Oct. 10, 2003, now U.S. Pat. No. 7,632,512, which is the U.S. national stage of international application no. PCT/GB01/05061, filed Nov. 16, 2001. Priority is claimed based on United Kingdom patent application no. GB 0028130.3, filed Nov. 17, 2000.

FIELD OF THE INVENTION

The present invention relates to polypeptides, polynucleotides and compositions thereof for use as medicaments, particularly to inhibit or prevent cell growth, such as bacterial cell growth.

BACKGROUND TO THE INVENTION

Spore-forming bacteria form a relatively small class of bacteria which are capable of producing endospores. Endospores are dormant non-reproductive survival forms of the bacteria which are resistant to inhospitable environments such as high temperatures, harmful chemical agents and damage from UV light. These spore-forming bacteria comprise *Bacillus, Clostridia* and *Sporosarcina* species as well as one strain of *Thermoactinomyces* and other less common species of *Sporolactobacillus* and *Oscillospira*. During a process of sporulation a class of proteins known as the small acid-soluble spore proteins (SASP) are produced. SASP are acid-soluble and have low molecular weights of between 5 and 11 kDa. SASP are reported to have two main roles within bacterial spores: firstly, they act to protect the spore DNA from damage from UV, heat, depurination and many potentially harmful chemical agents; and secondly, SASP provide a source of free amino acids upon spore germination, without which the newly vegetative cells cannot outgrow.

In *Bacillus* species there are three types of SASP known as α, β and γ type SASP. The amino acid sequences of a/(3-type SASP are highly conserved both within and between species (~70% identity and ~80% similarity, without gaps for *Bacillus* species). However these proteins show no sequence similarity to any other protein family and do not contain any motifs characteristic of other DNA binding proteins (Setlow, 1988). The α/β-type SASP are closely related immunogenically, have molecular weights of approximately 6.2-7.6 kDa and have a significant percentage of hydrophobic amino acids (up to 30%) (Setlow, 1988). The γ type SASP have a molecular weight of 8-11 kDa, are extremely low in large hydrophobic amino acids (<11%) and have a higher isoelectric points than the α/β type SASP from the same species (Setlow, 1988). In any given organism there are two major SASP of the α/β type, as well as many minor α/β type SASP, each encoded by a unique gene (Setlow, 1988). In contrast, all the organisms which have been examined have only one γ type SASP and its function is quite different to α/β type SASP, being used primarily to supply amino acids for outgrowth (Hackett and Setlow, 1987). A list of all the α/β type SASP which have been sequenced to date are given in Appendix 1, together with their related protein sequences. The extent of conserved amino acid residues between these protein sequences is shown in Appendix 2.

Various studies on SASP have focused on characterising the way in which the α/β type SASP protects DNA from UV damage. In one study (Setlow et al 1991) a gene (sspC) encoding an α/β-type SASP was inserted in a plasmid under the control of an inducible promoter to show that SASP cause DNA of a vegetative cell to assume spore-like characteristics. It was observed that binding of α/β type SASP to *E. coli* DNA caused an increase in plasmid negative superhelical density suggesting a concomitant change in DNA structure. It is postulated that a change in conformation of DNA from B-like to A-like protects the DNA against UV light.

In the field of medicine, regulation of cell growth is a fundamental concern. Cell growth within the body is subject to strict control; this includes both the cells which comprise the body's tissues and organs as well as commensal bacterial cells such as the skin and gut flora. Uncontrolled growth of microorganisms such as bacteria or fungi can be problematic or life threatening to a patient. Common treatment for bacterial infections in particular, involves the use of conventional antibiotics which may have a broad spectrum of activity (such as penicillin) that usually work by targeting bacterial cell walls. Other classes of antibiotics act by inhibiting protein synthesis in the bacterial cell, although many of these also display varying levels of toxicity to human and other animal cells. Bacteria can readily become resistant to conventional antibiotics and "super resistant" strains are now emerging. Thus there is a clear need for alternatives to currently available antibiotics.

Under certain circumstances normal cells in the body's tissues or organs can adopt aberrant characteristics and undergo uncontrolled growth, leading to the disease cancer, which can be life threatening. Many of the current treatments for cancer involve the use of agents or drugs which have toxic and/or unpleasant side effects. Some cancers also exhibit resistance to drugs or do not respond to other treatment regimes, thus alternative control measures are urgently needed.

SUMMARY OF THE INVENTION

In a first aspect, the present invention provides a polypeptide having α/β type SASP activity, for use as a medicament.

It has surprisingly been found that the polypeptide of the present invention may be used as a medicament, particularly to inhibit or prevent unwanted cell growth such as cell growth which is pathogenic to a subject. Such cell growth includes growth by bacterial cells, and some eukaryotic cells such as fungal or cancer cells.

A polypeptide according to the present invention may comprise any peptide, oligopeptide, protein and may exist in monomeric or multimeric form with or without covalent modification such as post-translational modification including glycosylation. Typical polypeptides according to the present invention comprise the amino acid sequence:

(SEQ ID NO: 1)
mannnssnsnellvpgaeqaidqmkyeiasefgvnlgadttarangsvgg eitkrlvqlaeqqlgggtk.

Preferably, the polypeptide comprises any one of the amino acid sequences shown in appendix 1 such as that encoded by the sspC gene from *Bacillus subtilis*, as shown in appendix 3. Any one of these polypeptides may contain mutations and/or those produced by random mutagenesis or by site directed mutagenesis, which do not substantially reduce the α/β type SASP activity thereof. Despite the high degree of sequence conservation between natural SASP proteins, significant differences in DNA affinities exist (Setlow et al., 1992). The potential exists to tailor SASP protein sequences to increase affinity of the protein for target DNA. On this basis it may be possible to utilise the natural variation in SASP or to engineer SASP to optimise targeting of different species of bacteria and/or desired genes within any given organism.

Generally, α/β type SASP activity may be measured by evaluating the effect of the polypeptide on DNA conformation. α/β type SASP activity may therefore be defined as the ability to convert DNA from a B-like conformation to an A-like conformation. This may be measured by any one of the following techniques.

(a) A reference for describing the change in conformation from B- to A-like is Mohr et al., 1991. Changes in circular dichroism spectra have long been regarded as sensitive criteria for DNA conformations and distinctions between the main families of secondary structure are unambiguous (Mohr et al., 1991). Interaction of both eukaryotic (calf thymus) DNA and prokaryotic DNAs with α/β-type SASP (in particular experiments using SspC from *B. subtilis*) induces spectroscopic features characteristic of A-DNA. Fourier-transform infrared (FTIR) spectroscopy provides an independent means of evaluating the conformational state of DNA complexed with α/β-type SASP. The FTIR spectra of concentrated solutions of calf thymus DNA show a principal absorption band at 1225 cm$^{-1}$ which arises from the antisymmetric O-P-O phosphate stretching vibration (Mohr et al 1991). This band shifts to 1246 cm$^{-1}$ with SspC-calf thymus. Such behaviour is characteristic of a B- to A-transition, although it should be noted that hydration effects alone can also influence the position of this O-P-O stretching band. Therefore an additional indication of B- to A-transition can be used, comprising the appearance in the FTIR spectrum of the SASP-DNA complex (a 1:1 ratio) of an absorption band at 1185 cm$^{-1}$. This is a specific marker for the A conformation of DNA since neither the B- or C-form of DNA produce an infra-red band at 1185 cm$^{-1}$ (Phole and Fritzsche, 1980). Hydration effects do not influence or affect the analysis of the 1185 cm-1 band. FTIR results show that, although dehydration can cause DNA to change conformation from B- to A-like, SASP promote this conformation change such that it reaches completion with significantly less reduction in humidity than is required for the process with DNA alone (Mohr et al, 1991).

(b) Also, SASP bound to DNA will protect DNA from degradation by DNase (Setlow et al., 1992). Two assays are possible to show that SASP bound to DNA in vitro protects a nucleic acid from nuclease digestion. The first, an electrophoretic assay, is the most straightforward. Briefly, nucleic acid (including pUC19 and pUB110) is incubated with various amounts of SASP for 1 hour at 37° C. At this point DNase I (or *S. aureus* nuclease) is added and incubation carried out for a further 15 min before adding SDS/EDTA followed by NaCl and ethanol to precipitate the DNA. The precipitated DNA is analysed by agarose (2%) (for polynucleotides) or acrylamide (oligonucleotides) gel electrophoresis. Protection of both pUC19 and pUB110 is evident at a ratio of SASP to DNA of 1:1 and is maximal at a ratio of 4:1. Analysis of DNase protection for four other α/β-type SASP indicate that these proteins also confer DNAse resistance to this plasmid. SASP-I from *Bacillus cereus* and SASP-A show similar patterns of protected bands whereas SASP-α and -β from Clostridia bifermentans give different patterns (Setlow et al., 1992). The second assay is an acid precipitation assay.

(c) SASP bound to DNA protects the DNA against cleavage by restriction enzymes, particularly those with specificity for GC-rich sequences (Setlow et al., 1992). Restriction enzyme digestions of pUC19 DNA bound by SspC (8:1 ratio of SspC to DNA) were carried out and digests analysed by agarose gel electrophoresis. For enzymes rich in AT sequence i.e. DarI (TTTAAA) inhibition was <10%. Increasing levels of GC content in the restriction enzyme recognition site led to increased protection by SASP with those enzymes recognizing GC-rich sequences (i.e. KpnI GGTACC) being inhibited >75%.

(d) Also SASP increase negative superhelical density of plasmids in the presence of topoisomerase I. The method for assaying this effect is given in Nicholson et al., 1990b. In summary, 1 μg samples of plasmid (pUC19 or pUB110) are incubated overnight in a 20 μl volume reaction mixture at 4° C. with various amounts of SspC, followed by topoisomerase I addition and further incubation for 2 h at 37° C. After deproteinization, samples are analysed by electrophoresis on agarose gels containing chloroquine (2 μg per ml). The average value of negative supertwists can be determined by comparing the position of the bands on the agarose gel with a set of standards prepared by incubating plasmid DNA with topoisomerase in the presence of differing amounts of ethidium bromide (Nicholas and Setlow, 1990). Maximum SspC binding results in introduction of a large number of negative supertwists in both plasmids. With 12 μg SspC added to the plasmid DNA approximately 18 and 38 supercoils are introduced in pUC19 and pUB110, respectively. Since pUC19 is approximately 60% the size of pUB110, the superhelical density induced in both plasmids by SspC binding is similar. Note that the binding of protein HU to DNA which does not induce a B-to-A conformation change in DNA only induces ~40% the number of negative supertwists per unit of DNA as does SspC (Nicholson et al., 1990).

(e) Also, SASP bound to DNA protects against the formation of cyclobutane-type thymine dimers upon UV irradiation, but promotes formation of spore photoproduct, an adduct between adjacent thymine residues (Nicholson et al., 1991). Yields of pyrimidine dimers and spore photoproduct (SP) were <0.2% and 8% of total thymine, respectively when DNA saturated with SASP was irradiated at 254 nm with 30 kJ/m2. In the absence of SASP the yields were reversed—4.5% and 0.3%, respectively (Nicholson et al., 1991). Yields of SP in vivo i.e. in spores and thymine dimers in vegetative cells are similar and extremely high (>25% of total thymine) (Donnellan and Setlow, 1965). UV irradiation of DNA in vitro also ordinarily produces fluorescent bipyrimidine adducts, cyclobutane type cytosine dimers and also cyclobutane dimers between cytosine and thymine as well as a 6-4 bipyrimidine adduct. The yields of all types of photoproduct are greatly reduced upon irradiation, in vitro, of DNA bound by α/β-type SASP (Fairhead and Setlow, 1991).

(f) It has also been demonstrated that α/β type SASP reduce the rate of depurination of DNA in vitro at least 20-fold. Three different procedures for measuring DNA depurination in vitro are given in Fairhead et al., 1993.

In a further aspect, the present invention provides a polynucleotide encoding a polypeptide as defined above, for use as a medicament.

In this aspect of the invention, whilst the polypeptide is thought to be the active species, delivery of the polynucleotide to target cells for expression therein may result in expressed polypeptide inhibiting or preventing growth of the cell.

The polynucleotide may be DNA or RNA, depending on the delivery system used. Whilst it is preferred for reasons of stability and ease of manipulation that the polynucleotide is DNA, if RNA is used it eliminates the possibility of SASP inhibiting its own production. In a particularly preferred embodiment, the DNA comprises the sspC gene from *B. subtilis*. Degeneracy of the genetic code allows mutations which do not alter the amino acid sequence of the expression production of the DNA.

The polynucleotide may be used for the preparation of a medicament for inhibiting or preventing cell growth in a number of ways. In one embodiment, the medicament comprises the polynucleotide, typically formulated for administration to a subject. In another embodiment, the polynucleotide is used to manufacture a medicament comprising the polypeptide. In a further embodiment, the medicament may be manufactured inside the target cell as the polypeptide.

Without wishing to be bound by theory, it is postulated that the polypeptide, when present in the target cell binds to the DNA of the cell and prevents replication of that DNA. The polypeptide may also completely or partially inhibit or prevent transcription of the DNA with which it is associated. In this way, further cell growth is inhibited or prevented. Particularly in the case of microbial cell infection, prevention or inhibition of growth allows the subject's immune system opportunity to deal with the infected cells. Another aspect is that binding of SASP to DNA could prevent cells from expressing genes involved in evasion of host immune systems.

In a further aspect, the present invention provides a composition for inhibiting or preventing cell growth comprising a polypeptide as defined above and a delivery system therefor. In a further aspect, the present invention provides a composition for inhibiting or preventing cell growth comprising a polynucleotide as defined above and a delivery system therefor which is capable of targeting a cell.

The compositions according to the present invention can be used for both medicinal and non-medicinal purposes. Where they are used for medicinal purposes such as discussed herein, there is a need to ensure that the delivery system used is suitable to treat the relevant medical condition. It is preferred to use the polynucleotide-containing composition because this can be delivered to target cells by delivery systems which are based on polynucleotides such as viruses. Where the delivery system comprises a virus, the polynucleotide may be incorporated in the genome of the virus and may therefore use the viral cell targetting mechanisms to enter the cell so that the polypeptide can be expressed in the cell to take effect. Where the target cell is a eukaryotic cell, a eukaryotic virus such as adenovirus, HSV, HIV, may be modified and used or any other virus having a specific tropism for the target cell.

In a particularly advantageous embodiment of the present invention, the virus comprises a bacteriophage (i.e. a bacterial virus). Bacteriophages are generally capable of targeting bacteria and are usually very specific in that any species of bacteria will have its own unique range of bacteriophages. Moreover, each bacterial strain may well have at least one bacteriophage which is unique to that strain. Thus, using a bacteriophage as a delivery system ensures that no bacteria, other than those targeted, will be infected. A list of common pathogens and some of their bacteriophages is given in appendix 4.

There are various types of bacteriophage, including lysogenic phages such as lambda, filamentous phages or lytic phages, which are not lysogenic. Bacteriophages can comprise single stranded DNA or RNA, to which SASP is unable to bind, as well as the more common double stranded DNA such as lambda. It is preferred to use a bacteriophage which cannot establish lysogeny, or a lysogenic phage which has been treated so that a gene involved in establishing lysogeny is inactivated. In either case it is preferred to inactivate at least one of the genes encoding products involved in the lytic process. This is advantageous because prevention of target cell lysis prevents the toxic contents of the cell being released and adversely affecting the host. One drawback of conventional antibiotics is that once the antibiotics are administered to a subject, disruption of the bacterial cell wall can be fatal to the host due to a massive immune response to cell wall components. This problem is avoided by preventing bacterial cell lysis in accordance with the present invention.

Inactivation of a lysis gene is conveniently achieved by inserting into the gene the polynucleotide according to the present invention. This can have a further advantage in that expression of lysis genes occurs sufficiently late in the life cycle of the phage that many phage particles can be produced in a host cell before the polypeptide is expressed by the polynucleotide.

Typical lysis genes include the S gene of the bacteriophage lambda. This gene encodes a holin, which is a protein which forms pores in the host cell which then allows other lytic enzymes produced by the bacteriophage to cause lysis.

A polynucleotide of the present invention may be inserted within, or largely replace the S gene and preferably comes under control of the S gene promoter $P_R'$. Analogously, the polynucleotide may be inserted in one of the other genes involved in the lytic cycle such as the R gene. The R gene product is a lytic transglycosylase. In this case, the S gene may or may not be additionally disrupted. Equivalent genes in other types of bacteriophage can be used in an analogous way as locations for the polynucleotide when targeting bacteria other than *E. coli*.

In a further embodiment, the polynucleotide can be located elsewhere on the bacteriophage chromosome and placed under control of a bacteriophage or bacterial promoter. Optionally, production of one or more proteins involved in lysis could still be inhibited. Alternatively, the lytic cycle could be left to run its course. For example, it is possible to use bacterial promoters which react to cues found in a host under infection conditions such as temperature sensitive promoters, the P3 promoter of the *Staphylococcus aureus* agr locus, or other promoters involved in two component sensor regulator pathways. Further examples include promoters active under microaerophilic conditions, under low iron conditions or those stimulated by host specific factors such as nicotinic acid or magnesium ions.

In a further aspect, the virus may be modified to increase or alter its host specificity. In the case of bacteriophages, these may be engineered to infect cell types other than bacteria by modifying the tail to generate different affinities and/or ability to infect cells. For example, it has been shown that mammalian cell tropism can be conferred on filamentous bacteriophage by presenting a ligand that binds to a mammalian cell surface molecule on the coat protein of the bacteriophage (Larocca et al 1998). For example, it has been demonstrated that when a phage M13) is engineered to display genetically the growth factor ligand, FGF2 (as a fusion to its minor coat protein pill), it acquires the ability to deliver a gene to mammalian cells through the FGF receptor resulting in transduced cells (Larocca et al., 1999). Other workers have also reported similar findings using phage that display a single chain antibody (scFvc) directed against ErbB2, a member of the EGF (epidermal growth factor) receptor family (Poul and Marks, 1999). Selection of phage engineered for receptor-mediated gene transfer to mammalian cells can be enhanced by screening phage libraries for functional ligands capable of delivering DNA to cells (Kassner et al., 1999).

A barrier to Caudovirales (tailed bacteriophages) infecting cells other than their natural host is the lack of an appropriate receptor present on the surface of the target bacterium to which the phage can adsorb. By addressing this it is possible to create phages which contain the same modified DNA (i.e. SASP containing) but which can target broad host ranges. For example, a phage may be modified to allow it to target a receptor which is common in several species of bacteria. Alternatively, the modified phage DNA may be packaged into identical phage heads which have been given a variety of tails each expressing an affinity for receptors expressed by different bacteria. Bacteriophages can also express antibody fragments as fusion proteins. For example the filamentous phage M13 has been engineered to express a g3p-fusion protein comprising a *Helicobacter pylori*-antigen-binding single-chain variable fragment (ScFv) (Cao et al., 2000). This ScFv-phage decreased the cfu of all tested strains of *H. pylori*. It may also be possible to cause a target bacterium to express a chosen receptor. For example, it has already been shown that *Pseudomonas* species can be modified to express LamB receptors, which are the receptor for lambda bacteriophage (de Vries et al., 1984). The gene, lamB, encoding these protein receptors is introduced into *Pseudomonas* by means of a plasmid and inserts into the *Pseudomonas* chromosome by homologous recombination. Whilst it is not always practicable to transform cells with plasmids it is possible to deliver the lamB gene to any Gram negative bacteria by means of a modified lysogenic bacteriophage specific to the target. The lamB gene should be under the control of a strong bacterial promoter and the phage should be altered so that lysogeny is always established. Administration of this type of phage, then, will render *Pseudomonas* species liable to infection by subsequently administered SASP/lambda. Other such modified phages can be produced for each target species and will act to broaden the host range of any given bacteriophage containing SASP.

In these ways, it is possible to extend the range of bacteria that a SASP containing phage can target, at least within the broad categories of Gram positive or Gram negative bacteria.

Modified bacteriophage are commercially available which have been designed specifically with cloning or gene expression in mind and may comprise multiple cloning sites and inducible promoters inserted into non-essential regions.

There are two classes of lambda cloning vectors: insertion vectors accept 0-12 kb DNA and include Lambda ZAPII, Uni-ZAP XR, and Lambda ZAP-Express (Stratagene); replacement vectors accept 9-23 kb and include Lambda FIXII and Lambda DASHII (Stratagene). Bacterial protein expression kits allowing expression of toxic genes are also available including the Lambda CE6 bacteriophage carrying the T7 RNA polymerase gene for delivery to *E. coli* strain BL21 cells (Stratagene). Bacteriophages with natural mutations within the S gene are used commercially to manufacture large quantities.

When used as a medicament, the polypeptide or polynucleotide of the present invention may be used for human therapy and may treat various conditions, especially microbial infections. Amongst those microbial infections which are treatable according to the present invention are topical infections, dental caries, respiratory infections, eye infections and localised organ infections. The invention is applicable to both human and animal therapy and may, for example, be used to treat systemic or topical infections in fish. Medicaments or pharmaceutical compositions may therefore be formulated according to the invention depending upon the use to which the polypeptide or polynucleotide is put. Typically, a medicament may be formulated which comprises the active ingredient optionally together with a pharmaceutically-acceptable excipient, diluent or carrier. The exact nature and quantities of the components of such pharmaceutical compositions may be determined empirically and will depend in part upon the route of administration of the composition. Routes of administration to recipients include oral, buccal, sublingual, by inhalation, topical (including ophthalmic), rectal, vaginal, nasal and parenteral (including intravenous, intra-arterial, intra-muscular, subcutaneous and intra-articular) For convenience of use, dosages according to the present invention will depend on the site and type of infection to be treated or prevented. For example, treatment of respiratory infections would be infected by a SASP/phage suspension administered by inhalation. Treatment of eye infections would be effected by use of a SASP/phage suspension administered by eye drops and so on. A mouthwash or toothpaste may be used in the treatment of dental caries which contains a SASP/phage formulation to eliminate bacteria associated with dental plaque formation. Accordingly, oral hygiene products containing polypeptide or polynucleotide according to the present invention are also provided.

The polypeptide, polynucleotide and compositions thereof according to the present invention may be used in non-medical applications as well. In a further aspect there is provided use of a polypeptide or polynucleotide as defined herein as a microbial decontaminant, more particularly a bacterial decontaminant which may be used to treat surface microbial contamination, may be used in land remediation or in water treatment. For example, the polynucleotide or polypeptide may be used in the treatment of medical personnel as a decontaminating agent, for example as a hand wash. Treatment of work surfaces and equipment is also provided, especially that used in hospital procedures or in food preparation. This has an advantage over conventional antibacterial chemicals which can damage delicate instruments and may be undesirable in food preparation areas. As a further example of surface microbial decontamination, the invention may be used in the topical treatment of carcasses. In the treatment of water, the present invention may be effective against water borne pathogens, especially *Vibrio cholerae*, *Legionella pneumophila*, *Salmonella typhi* and *Shigella dysenteriae*. Microbial contamination of land may equally be combated according to the present invention.

In a further aspect, there is provided use of the polypeptide or polynucleotide as an antimicrobial agent, particularly an antibacterial or antifungal agent, in the treatment of plant material such as plants, for example crops, or in the treatment of seeds or grain produced therefrom. Fruits may be sprayed with phages against bacteria causing soft rots. Microorganisms such as *Erwinia* species may be treated in this way. Ornamental plants such as geraniums are susceptible to bacterial blight caused, for example, by *Xanthomonas campestris*; this organism also affects tomatoes. Similarly *Pseudomonas* species which infect beans and mushrooms can also be treated according to the present invention.

In a further aspect, the polynucleotide or polypeptide may be used to treat vermin such as rats so as to eliminate specific bacteria therefrom. A common treatment to eliminte rats is the administration of feed containing anticoagulant substances such as warfarin. The antidote to such substances is commonly vitamin K. Vitamin K is produced in the mammalian gut by bacteria. Resistance to anticoagulants by rats is acquired due to colonisation of the gut by bacteria which produce elevated levels of vitamin K. Therefore the treatment of vermin according to the present invention allows conventional anticoagulant administration to be successful in vermin control.

The invention will now be described in further detail, by way of example only, with reference to the accompanying drawings and the following examples and appendices.

EXPERIMENTAL PROCEDURES

Figure 1:
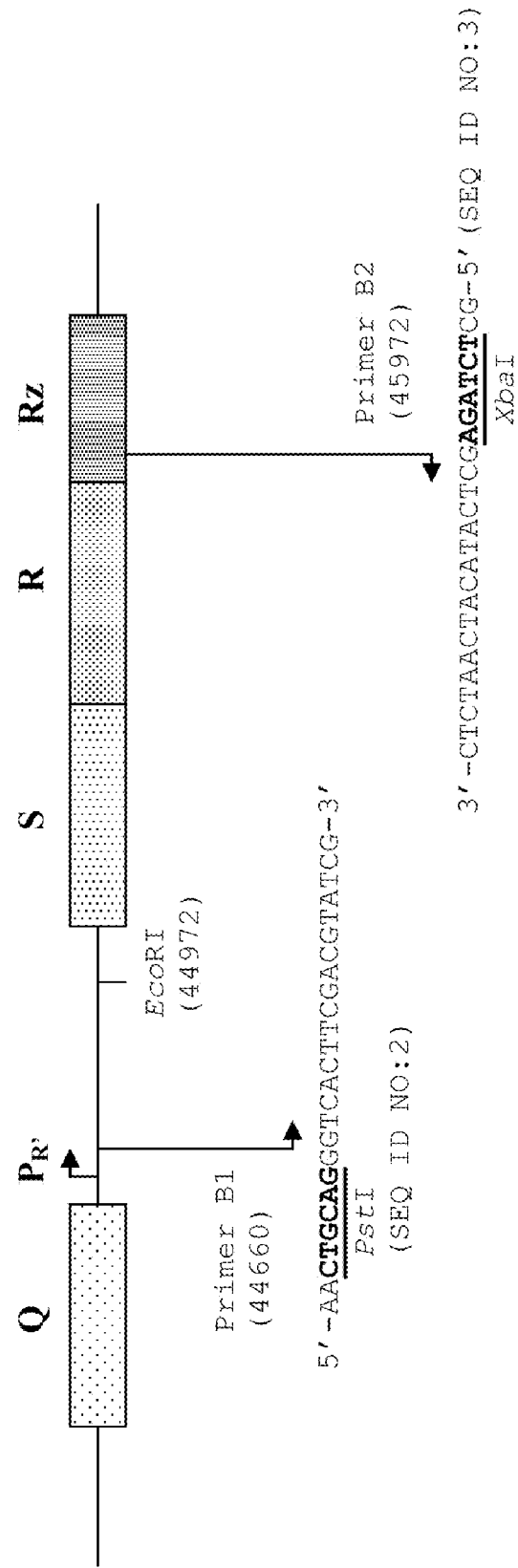
FIG. 1 shows a diagrammatic representation of part of the lambda genome, spanning the S gene.

All experimental procedures are standard as described in Sambrook et al. (1991) unless stated otherwise.

Restriction digestions were carried out in a total volume of 50 μl, using 2 μl of each enzyme, and incubated at 37° C. for 4 h, unless otherwise stated.

Dephosphorylation of template DNA was carried out in a total volume of 50 μl using 10× buffer (5 μl) and alkaline phosphatase (2.5 U) (5 μl) with incubation at 37° C. for 1 h.

Ligations were carried out in a total volume of 10 μl using 3 Weiss Units (1 μl) of T4 DNA ligase and were routinely performed at 16° C. overnight.

PCR mixes were routinely made up as follows (total volume of 100 μl):

| Template DNA | 0.1 μg plasmid or purified lambda DNA/1 μg chromosomal DNA/1 colony |
|---|---|
| 10X Buffer (with 1.5 mM MgCl$_2$) | 10 μl |
| dNTP mix (10 mM stock) | 2 μl |
| Taq Polymerase (2.5U) | 1 μl |
| Primers (Forward and Reverse) | 100 pmoles of each |
| Adjust to a final volume of | 100 μl with dH$_2$O |

PCR reactions were carried out as follows: (unless otherwise stated)

| | |
|---|---|
| 95° C. for 3 mins (denature) | |
| 94° C. for 30 sec (denature) | |
| 58° C. for 30 sec (anneal) | for 25 cycles |
| 72° C. for 30 sec per kb of DNA (extend) | |
| 72° C. for 10 mins | |

Primers were obtained from Gibco BRL or Sigma Genosys. Where primers include recognition sequences for restriction enzymes, the preferred upstream sequence of each enzyme (PCR Essential Data, 1995) was included.

A In Vitro/In Vivo Production I

1. A fragment of the lambda genome, spanning the S gene, was amplified by PCR using primers with suitable restriction enzyme sites at the 5' end to allow directional ligation into a general E. coli cloning vector such as pUC18 or pBluescript (Stratagene). Thus, Primer B1 comprises the restriction enzyme recognition sequence of PstI followed by sequence of lambda from base 44660 to base 44677 (FIG. 1). Primer B2 includes the restriction enzyme recognition sequence of XbaI followed by the reverse and complement of lambda sequence from base 45972 to base 45956 (FIG. 1), for example:

```
                                          (SEQ ID NO: 2)
Primer B1:  5'-AACTGCAGGGTCACTTCGACGTATCG-3'

(SEQ ID NO: 3)
Primer B2:  5'-GCTCTAGAGCTCATACATCAATCTC-3'
```

In FIG. 1, the position of the late genes involved in lysis, together with the P$_{R'}$ promoter are shown relative to each other. The position of primers B1 and B2, together with the EcoRI restriction enzyme site, are also shown.

Figure 2:
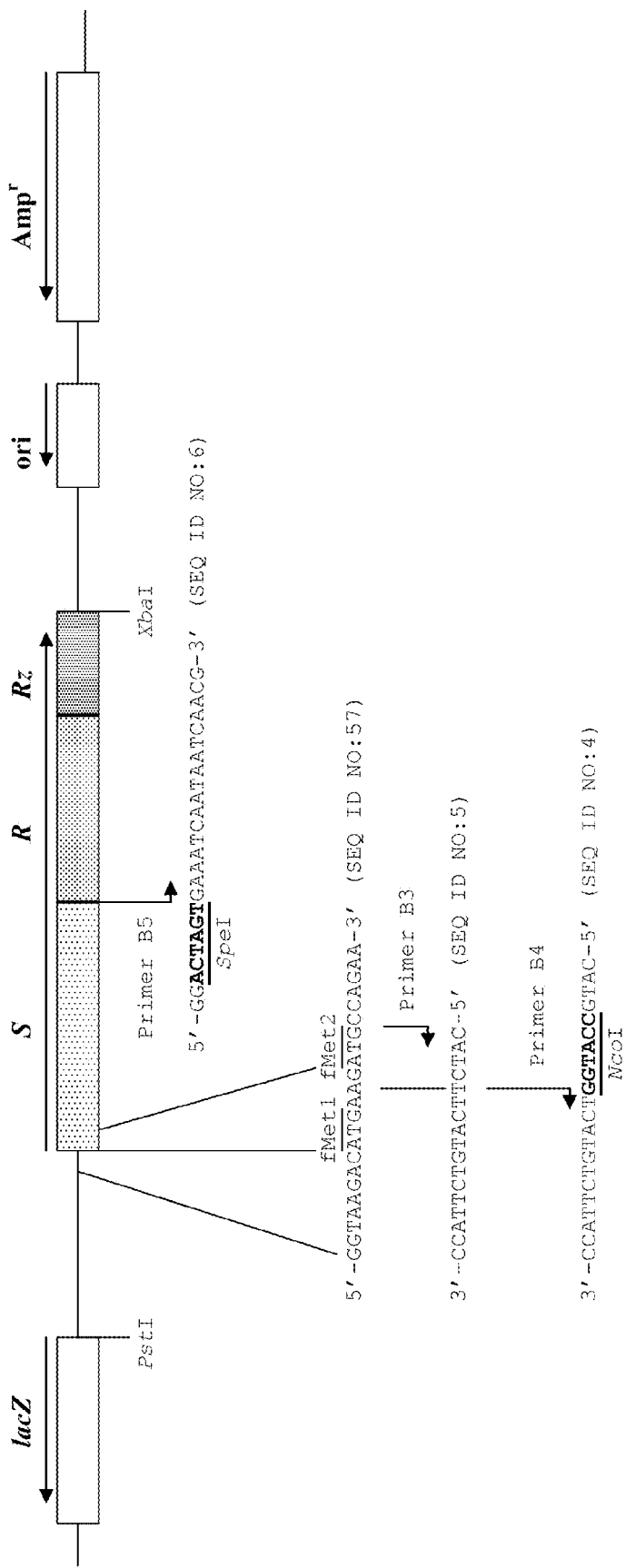
FIG. 2 shows a map of pB/LF1.

2. The resulting 1328 bp PCR product was digested with PstI/XbaI and ligated with similarly digested, dephosphorylated pBluescript to give pB/LF1 (FIG. 2). FIG. 2 shows a linear map of pB/LF1 showing the plasmid backbone of pBluescript SK (+) (Stratagene) and the position of the lambda fragment insert bordered by PstI/XbaI restriction sites (see FIG. 1). The sequence spanning the start of the S ORF is given together with the position of the ribosome binding site (rbs), and the first and second start codons. The relative positions and sequences of the inverse PCR primers are shown. Primer B3 produces a PCR product which is blunt ended at the 5' end. Primer B4 produces a PCR product which, following digestion with NcoI, has a 5' end overhang.

3. Plasmid pB/LF1 was introduced into E. coli by electroporation and putative recombinants were recovered as white colonies on LB agar plates in the presence of X-gal (80 μl, 20 mg/ml) and ampicillin (50 μg/ml). A correct transformant was identified following restriction digestion of the plasmids with EcoRI, resulting in two fragments of approximately 300 bp and 3950 bp.

4. The S gene of lambda is a dual start gene, with transcription from the second fMet start codon resulting in a 2-fold greater level of protein. Therefore, the chosen SASP gene, in this instance sspC from B. subtilis, was inserted in frame with this second start codon. Inverse PCR of plasmid pB/LF1 was carried out (with an extension time of 4 min 30 sec at 68° C.) using reverse primers to produce a fragment with a 5' end overhang. The restriction enzyme NcoI has a recognition sequence (CCATGG) which incorporates the nucleotides ATG. By adding the NcoI recognition sequence to the front of template (pB/LF1) and insert (sspC) DNA primers it allows subsequent ligation of these PCR products so that the sspC gene is in frame with the start codon of the lambda S gene.

The reverse primer (B4) is the complement of lambda sequence starting at the third nucleotide 5' of the second ATG start codon of the S gene (FIG. 2). The primer contains the recognition sequence of the restriction enzyme NcoI, for example:

```
                                        (SEQ ID NO: 4)
    Primer B4: 5'-CATGCCATGGTCATGTCTTACC-3'
```

It is possible to replace the S gene with a SASP gene by blunt end ligation and in this case a reverse primer which begins at the complement of the second ATG start codon of the S gene (FIG. 2) can be used, for example:

```
Primer B3: 5'-CATCTTCATGTCTTACC-3'     (SEQ ID NO: 5)
```

The forward primer was based on sequence at the beginning of the lambda R gene from base 45499 to base 45515 (see FIG. 2). The recognition sequence for restriction enzyme SpeI was used in front of the lambda sequence to allow directional ligation with the sspC gene, for example:

```
                                        (SEQ ID NO: 6)
    Primer B5: 5'-GGACTAGTGAAATCAATAATCAACG-3'
```

5. The sspC gene was PCR amplified (using 20 sec extension time) in such a way as to enable ligation to either of the inverse PCR products obtained from primers B3 and B5, or B4 and B5, for example:
   (i) to ligate to the pB/LF1 inverse PCR product produced using primers B3 and B5 (to give plasmid pB/SAPB), a forward primer should be used which begins with the nucleotide immediately 3' of the ATG start codon of the sspC gene (FIG. 3), for example:

```
                                        (SEQ ID NO: 7)
    Primer B6: 5'-GCTCAACAAAGTAGATCAAG-3'
```

Figure 3:
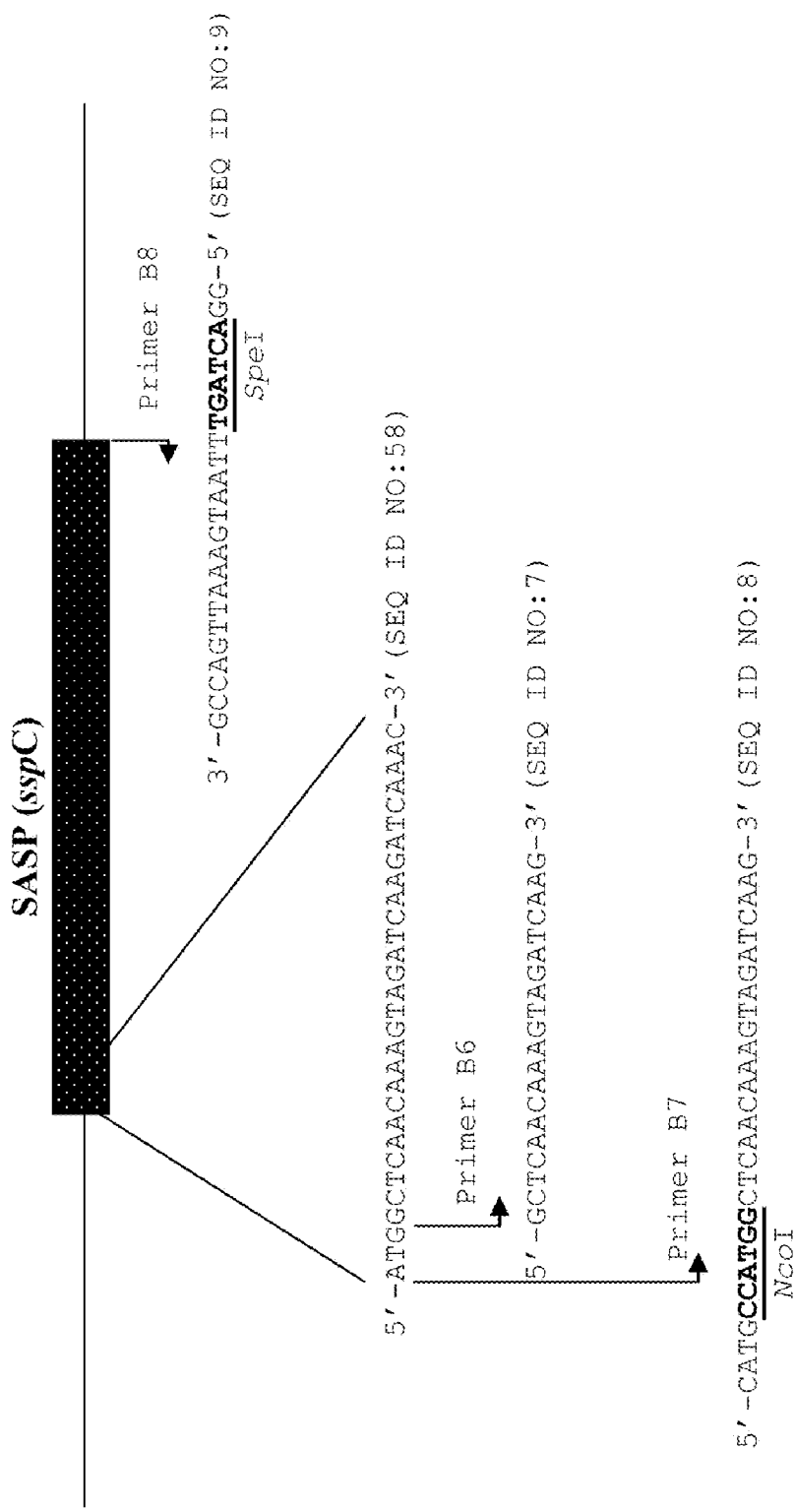
FIG. 3 shows a diagrammatic representation of part of the Bacillus subtilis genome spanning the sspC gene.

(ii) to ligate to the pB/LF1 inverse PCR product produced using primers B4 and B5 (to give plasmid pB/SAPO), a forward primer comprising the sequence of sspC starting at the 5th nucleotide of the sspC ORF was used (FIG. 3). This primer has an NcoI restriction enzyme sequence immediately prior to the sspC sequence, which in fact incorporates the first four nucleotides of the sspC gene itself, for example:

```
                                        (SEQ ID NO: 8)
Primer B7: 5'-CATGCCATGGCTCAACAAAGTAGATCAAG-3'
```

The reverse primer is the complement of sequence at the end of the sspC ORF, i.e. to produce a PCR product which includes the stop codon of the sspC gene (FIG. 3). The primer includes SpeI sequence to allow directional ligation with either inverse PCR product of pB/LF1, for example:

```
                                        (SEQ ID NO: 9)
    Primer B8: 5'-GGACTAGTTTAATGAAATTGACCG-3'
```

In FIG. 3, sspC gene is shown together with the relative positions of the PCR primers, B6, B7 and B8. Primer B6 will produce a PCR product with is blunt ended at the 5' end. Primer B7 produces a PCR product which, following digestion with NcoI, will have a 5' overhang.

6. The PCR amplified sspC gene (from primers B7 and B8) and inverse PCR amplified pB/LF1 (from primers B4 and B5) were digested with the restriction enzymes NcoI and SpeI. Digested linear pB/LF1 inverse PCR product was dephosphorylated prior to ligation.

Figure 4:
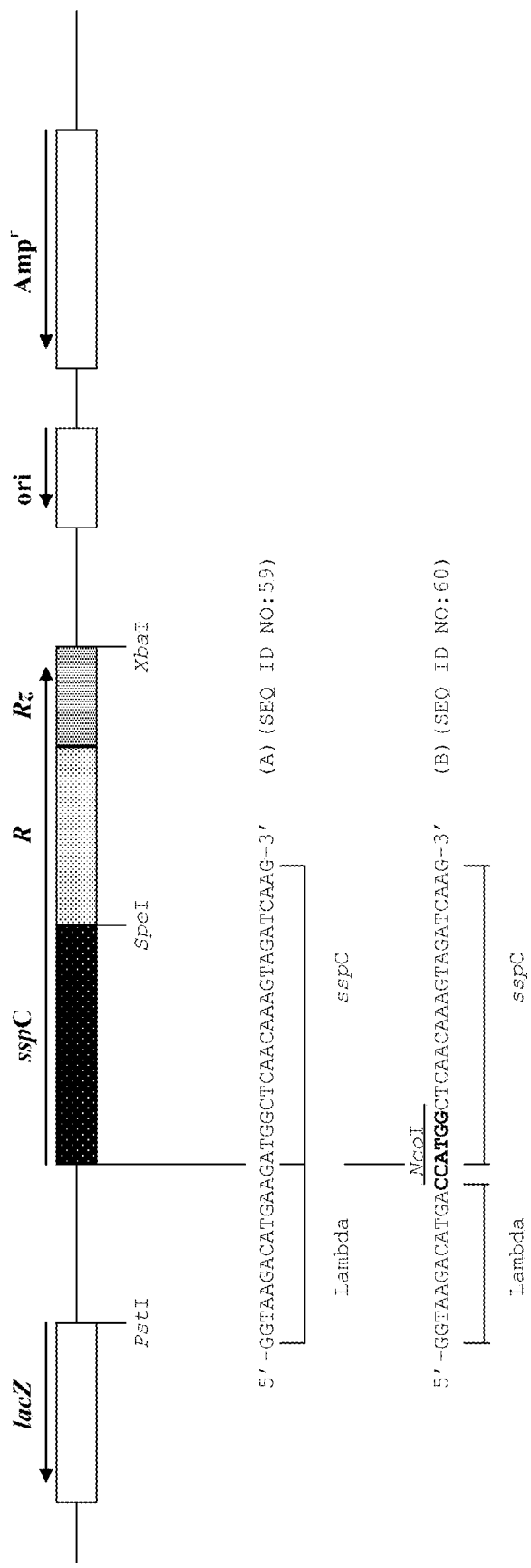
FIG. 4 shows a map of (A) pB/SAPB and (B) pB/SAPO.

7. After cleaning of digested DNA, ligations were carried out to give plasmid pB/SAPO in which the sspC gene largely replaces the S gene of lambda (FIG. 4). For plasmid pB/SAPB PCR products are simply ligated together (FIG. 4). FIG. 4 shows a linear map of (A) pB/SAPB or (b) pB/SAPO. These plasmids are constructed following insertion of the sspC gene into inverse PCR amplified plasmid pB/LF1 (amplified using primers B3 and B5 or B4 and B5 (see section A 4)).

(A) Linear map of pB/SAPB showing inverse PCR amplified pB/LF1 (from primers B3 and B5) containing the sspC gene. The sequence given spans the S gene ribosome binding site and start of the sspC ORF, joined by blunt end ligation. Linear map of pB/SAPO showing inverse PCR amplified pB/LF1 (from primers B4 and B5) containing the sspC gene. The sequence given spans the S gene ribosome binding site and start of the sspC ORF, joined by ligation following digestion with NcoI.

Figure 5:
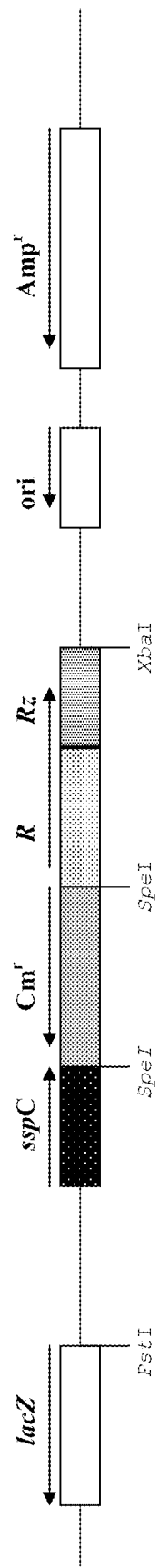
FIG. 5 shows a map of pB/SAPOC.

8. It is possible to produce a lambda carrying a SASP gene with, or without an antibiotic resistance gene present. Use of an antibiotic resistance gene provides a selectable marker to track the presence of a SASP gene and this has been carried out using a chloramphenicol resistance ($Cm^r$) gene. A $Cm^r$ gene (with its own promoter) has been inserted, in the opposite orientation, at the 3' end of the sspC gene following digestion of pB/SAPO with SpeI. This resulted in plasmid pB/SAPOC (FIG. 5). FIG. 5 shows a linear map of pB/SAPOC showing pBluescript backbone and the position of the sspC and $Cm^r$ genes within the lambda fragment bordered by PstI/XbaI restriction sites.

9. One method of producing SASP/lambda is to infect a strain of E. coli carrying pB/SAPOC with phage lambda. As the phages reproduce, the lambda/sspC/$Cm^r$ fragment within pB/SAPOC will become incorporated into some lambda genomes. This method has successfully been employed using a temperature sensitive (ts) lambda. This type of lambda can be stably maintained, as a prophage, within an E. coli chromosome at 30° C. but not at 42° C. The pB/SAPOC-bearing strain was grown in LB (containing 10 mM $MgSO_4$+0.2% maltose (w/v)) until the $OD_{600}$ reached 0.3. An aliquot (100 µl) was removed and mixed with 100 µl of lambda phage preparation. The mix was incubated without shaking at RT for 20 min, 3.5 ml molten top agar (LB 0.6% agar containing 10 mM $MgSO_4$+0.2% maltose (w/v)) held at 45° C., was added and poured onto pre-warmed LB agar plates. Plates were incubated overnight at 37° C. before LB (3 ml) was added onto the surface of the top agar. The top agar containing the plaques was transferred into 50 ml centrifuge tubes and stored at 4° C. overnight. Chloroform (250 µl) was added and the tube was gently inverted several times to lyse any whole bacterial cells, prior to centrifugation (4,000 rpm, 10 min, RT). The resulting phage lysate supernatant was transferred to a sterile tube and used to infect a strain of E. coli which could be lysogenised i.e. NM522 or Y1089r⁻, by mixing 100 µl lysate with 100 µl E. coli culture grown to an $OD_{600}$ of 0.3. Following incubation at RT for 30 min, 800 µl LB was added and the mix was plated out in 100 µl aliquots onto LB agar plates supplemented with chloramphenicol (10 µg/ml). Following incubation at 30° C. overnight $Cm^r$ colonies were isolated and examined for the presence of sspC-carrying lambda prophages.

Figure 6:
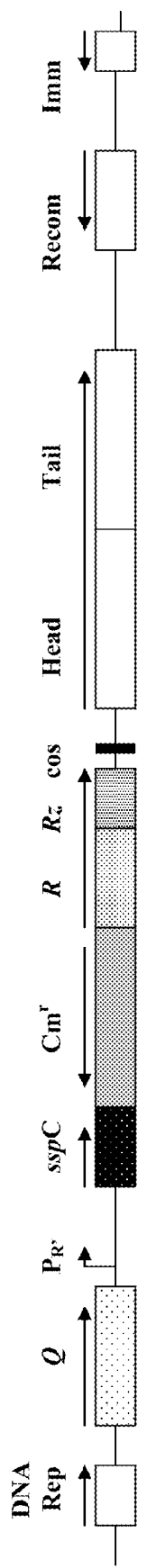
FIG. 6 shows a map of SSPC-lambda showing the substitution of the lambda S gene by the sspC gene from B. subtilis and insertion of a chloramphenicol resistance marker gene (Cm')

10. Cm resistant colonies were sub-cultured onto two LB plates containing chloramphenicol (10 µg/ml) and the plates were incubated at either 30° C. or 42° C. overnight. Colonies which had grown the following day at 30° C. but not at 42° C. were assumed to be lysogenic for recombinant lambda containing the sspC and Cm$^r$ genes. Colonies were also sub-cultured onto LB plates containing ampicillin to ensure that the whole pB/SAPOC plasmid had not integrated into the lambda genome. A strain of E. coli which was lysogenic, Cm resistant and ampicillin sensitive was identified and the prophage designated SSPC-lambda (FIG. 6). FIG. 6 shows a linear map of SSPC-lambda showing the substitution of the lambda S gene by the sspC gene from B. subtilis and insertion of a chloramphenicol resistance marker gene (Cm$^r$).

Figure 7:
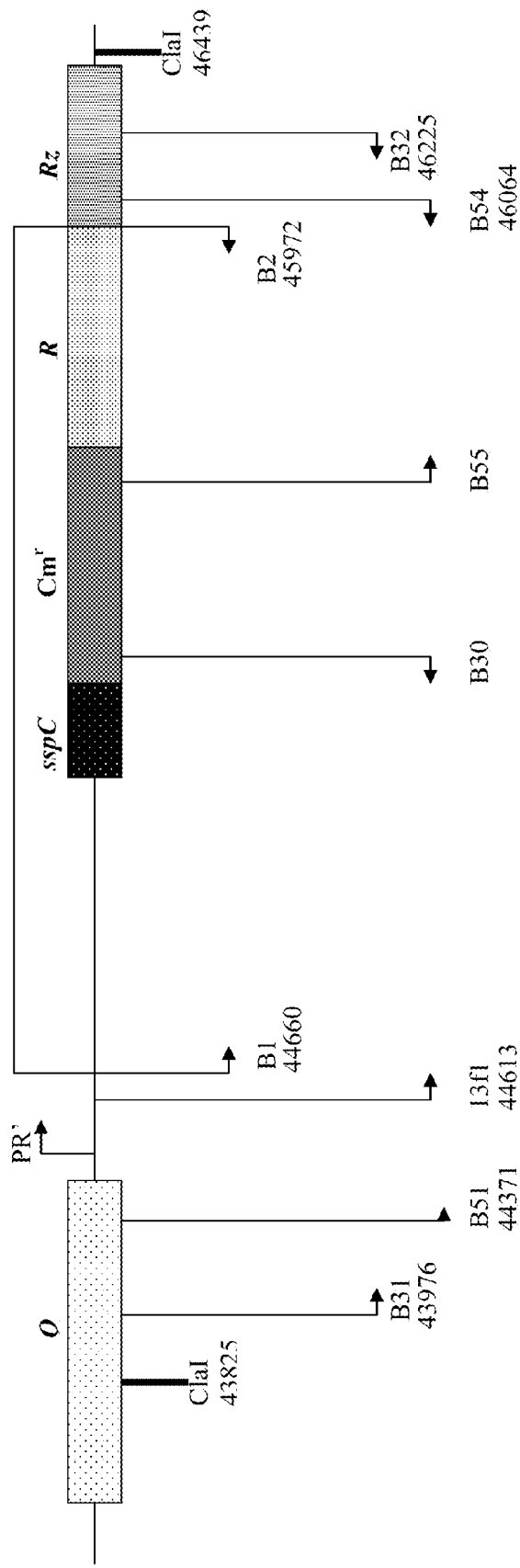
FIG. 7 shows a map of an area of SSPC-lambda genomic DNA with primer positions.

11. Sequencing reactions were carried out to confirm the presence, fidelity and orientation of the sspC and Cm$^r$ genes within the SSPC-lambda genome present in the host E. coli chromosome. Chromosomal DNA was prepared from the E. coli strain containing SSPC-lambda and digested with the restriction enzyme ClaI. This enzyme cuts at 15 sites within the lambda genome and an undetermined number of sites within the E. coli genome. Specifically, this enzyme cuts at bases 43825 and 46439 of the lambda genome, resulting in a fragment which spans the S and R lysis gene area of lambda bordered by primers B1 and B2 (FIG. 7). FIG. 7 shows an area of SSPC-lambda genomic DNA with primer positions:

position of primers B1 and B2 used to initially amplify lambda fragment to make pB/LF1 (section A 1)

position of ClaI sites showing extent of ligation product for PCR amplification and sequence verification (section A 11)

primers B31 and B32 used to PCR amplify region of lambda spanning B1-B2 fragment, for sequencing (section A 11)

primers 13f1, B30, B55 and B54 used for sequencing SSPC-lambda construct (section A 11).

Total digested DNA was then ligated overnight and an aliquot of the ligation mix (2.5 µl) was used as template DNA for a PCR reaction using the following programme:

| | |
|---|---|
| 95° C. for 3 mins (denature) | |
| 94° C. for 20 sec (denature) | |
| 62° C. for 30 sec (anneal) | for 10 cycles |
| 68° C. for 3 min 50 sec (extend) | |
| 94° C. for 20 sec (denature) | |
| 62° C. for 30 sec (anneal) | for 25 cycles |
| 68° C. for 3 min 50 sec + 10 sec | | extension time (extend)

72° C. for 10 mins

The following primers (B31 from base 43976 to 44000; B32 from base 46225 to 46203 of lambda) were used to produce a fragment of lambda DNA spanning the lambda/sspC/Cm$^r$ gene DNA which had originated from pB/SAPOC as a PstI/XbaI insert (FIG. 7).

```
                                        (SEQ ID NO: 10)
Primer B31:  5'-GGTACTGATGTGATGGCTGCTATGG-3'

(SEQ ID NO: 11)
Primer B32:  5'-GCAACATCATCACGCAGAGCATC-3'
```

The resulting PCR product was then used in several sequencing reactions using the following primers (see FIG. 7):

```
                                        (SEQ ID NO: 12)
Primer B30      5'-CAACAGTACTGCGATGAGTGG-3'

(SEQ ID NO: 13)
Primer 13f1     5'-GTAGTGAGATGAAAAGAG-3'

(SEQ ID NO: 14)
Primer 254      5'-GTAGGTAATGGCGTTATCACG-3'

(SEQ ID NO: 15)
Primer B55      5'-GGTGGTGCGTAACGGCAAAAGC-3'
```

12. It is also possible to produce a similar construct using a different ribosome binding site (rbs) upstream of the SASP gene as an alternative to the native S gene rbs. For example, the T7 phage gene 10 leader RNA can dramatically enhance the expression of some foreign genes in E. coli (Olins et al., 1988). Alternatively, the ribosome binding site sequence of the lambda V gene could be used as V encodes tail protein which is more abundant than the S gene product during the normal lytic life cycle of the bacteriophage lambda. In this instance, a construct has been produced using the native sspC rbs employing the same method as above, except the sspC gene was PCR amplified using a forward primer homologous to sequence approximately 40 bases upstream of the sspC start codon. A BamHI restriction enzyme site was included in front of the sspC sequence. For example:

```
                                        (SEQ ID NO: 16)
Primer B23:  5'-CGGGATCCGATTCAAACAAGCTTG-3'
```

Reverse primer B8 was used. The resulting PCR product was ligated with an inverse PCR amplified pB/LF1, amplified using forward primer B5, as previously, and a reverse primer, B21 with a BamHI restriction site in front of the pB/LF1 sequence:

```
                                        (SEQ ID NO: 17)
Primer B21:  5'-CGGGATCCCATCTTCATGTCTTTAC-3'
```

Production and identification of a strain carrying this form of lambda, designated SPPC-lambda, as a prophage was carried out as for SSPC-lambda. SPPC-lambda was also sequenced as described in section A 11 above.

13. Both SSPC- and SPPC-lambda constructs are maintained as prophages, that is they remain stably within their host E. coli chromosome. Only first generation mature phage particles have so far been used for infection. This helps to ensure comparability between each batch of mature phage produced. However, since it is not necessarily ideal to use a temperate, or lysogenising, phage for therapeutic purposes it is possible to alter the genes involved in establishing lysogeny so that they are inactive in an infective situation. In the system described here, the use of a temperature sensitive (ts) phage, means that lysogenisation is relatively rare at 37° C. or above. Of course, phage stocks themselves can also be maintained rather than lysogenic E. coli.

14. Preparations of both SSPC-lambda and SPPC-lambda were obtained by inducing the recombinant prophage-carrying strains to produce mature phage particles. Each strain was grown at 30° C. until the OD$_{600}$ reached 0.6 and then the temperature was shifted to 42° C. for 15 minutes. The culture was then incubated at 37° C., with shaking at 350 rpm to provide good aeration, for a further 3 h prior to harvesting by centrifugation (4,000 rpm, 10 min, RT). The supernatant was removed and the pellet resuspended in ⅕ volume of phage buffer. Chloroform (1/100 volume) was added to the resuspended cells and the suspension was mixed gently. The resultant lysate was centrifuged (4,000 rpm, 10 min, RT) and the supernatant transferred to a sterile tube and then stored at 4° C. The lysates were titred as described in section A 15, below.

15. To titre SSPC-lambda phage particles produced following induction, phage lysate was used to infect a non-lysogenising strain of *E. coli* containing a plasmid (designated pB/LF2) carrying a fragment of lambda DNA spanning the S and R lysis genes and $P_{R'}$ promoter. This promoter-containing fragment of lambda was PCR amplified using primer B51 (5'-AACTGCAGCGCTGTGACGATGCTAATCC-3' SEQ ID NO:18) from base 44371 to base 44390 and primer B2 (previously described) (see FIG. 7). The presence of reproducing lambda phages within the pB/LF2-bearing strain allows expression of the lysis gene cassette downstream from the plasmid based $P_{R'}$ promoter. The lysis genes' products expressed from the plasmid facilitate lysis of the bacteria and the formation of plaques. Phage titre is determined by plaque enumeration at the dilution where plaques are discrete and easily observable. Infection was carried out by growing the strain containing pB/LF2 to an $OD_{600}$ of 0.3 in LB containing 0.2% maltose, 10 mM $MgSO_4$ and 1ag/ml ampicillin. An aliquot (100 µl) of the cell culture was incubated with 100 µl of dilutions of SSPC phage lysate for 20 min at RT and then mixed with top agar and plated out as described in section A 9. There is up to a 5-log reduction in the titre of SSPC-lambda particles, compared to the parental lambda from which it is derived. Following the described protocol the parental lambda can produce approximately $10^{15}$ pfu per ml.

B In Vitro/In Vivo Production II

There are alternative methods for obtaining lambda containing a SASP gene in place of the lambda S gene, based on transforming a lambda lysogen with pB/SAPO or pB/SAPB (see section A above). In this case, competent cells should be prepared of a restriction⁻/modification⁺ strain of *E. coli* which is a lambda lysogen, for example MOB145.

1. Electro-competent lysogenic *E. coli* cells should be transformed with either pB/SAPO or pB/SAPB, or a suicide vector containing the equivalent lambda/sspC fragment of DNA. The transformed cells are allowed to recover for 1 h in SOC at 37° C. then centrifuged (4000 rpm, 10 min, RT). The pelleted cells should be resuspended in LB (1 ml) and 50 µl removed and made up to 1 ml with sterile LB. Cells should be plated out onto LB agar in 200 µl aliquots and incubated overnight at 37° C. The remaining 950 µl should be flash frozen in 50 µl aliquots and stored at −20° C.

2. There are several ways in which to select for double crossover event between the lambda fragment carried in the pB/SAPB or pB/SAPO plasmids and homologous sequence within the lambda genome. The use of a suicide vector can encourage double cross-over event since the vector cannot be maintained within the *E. coli* lysogen. Colonies of strains carrying potentially recombinant lambda prophages obtained from overnight growth on LB agar plates (see section A 9 above) can be PCR screened using primers which are based in the sspC gene and lambda, i.e. B1 and B8 or B2 and B7 (see section A). The resulting PCR product using either primer pair should be approximately 1.3 kb. Alternatively, a method based on induction of the lambda prophage can be employed since SASP-containing phage will no longer have a functional S gene and will not be able to lyse their host cells. Screening can be carried out by either:

i) UV irradiation of transformed cells according to Hendrix et al. (1983). Resuspend an aliquot of cells (20 µl) from above (step 9) to a maximum cell suspension of $2 \times 10^8$ cfu in 10 ml of a suitable non UV absorbing suspension medium (e.g. M9a or PBS) in a standard petri dish (9 cm). Irradiate cells using a UV light source (maximum output 260 nm). Following irradiation, induced cultures are incubated in M9a medium at 37° C. with aeration (if PBS is used as the suspension medium, fresh sterile growth medium (1/10 volume of 10×M9a is added). Photoreactivation is prevented by protecting the irradiated bacteria from visible light.

ii) Induction of thy⁻ lambda lysogens by thymidine starvation, according to Hendrix et al. (1983). Isolate thy mutants (Miller, 1972): The lysogenic strain should be grown in M9a medium supplemented with 10 µg/ml thymidine until $2 \times 10^8$ cfu/ml. Cells should be washed and resuspended in thymidine free M9a medium and then incubated at 37° C. for 2 h. Thymidine (10-25 µg/ml) should then be added to the culture and a further incubation for 90-120 min at 37° C. carried out.

iii) Temperature shift induction (if lambda cIts lysogen is used) as described in section A.

3. Cells should be allowed to grow for ~2 hours (in the presence of 0.2% glucose to reduce numbers of any free (and therefore potentially SASP-free) phage binding to unlysed bacterial cells). Any free phage must be separated out from cells which potentially contain the SASP/bacteriophage, by centrifugation (4,000 rpm, 10 min, RT). Pelleted cells should be resuspended in LB containing 0.2% glucose and incubation continued for approximately 1 h. Cells should be centrifuged (4,000 rpm, 10 min, RT), resuspended in LB (2 ml) and then lysed with chloroform (0.02 ml). Mature phage released from cells following chloroform-induced lysis should be separated from cellular debris by centrifugation (4,000 rpm, 15 min, RT).

4. Bacteriophage containing SASP should be enriched and purified by a suitable method. One such method is to infect a growing culture of susceptible *E. coli* cells with SASP-lambda and repeat step B 3 above.

5. The presence of recombinant lambda should be verified by isolating DNA from putative SASP-lambda constructs and carrying out PCR screening to confirm the presence of the SASP gene using appropriate primer pairs, as discussed in section B 2. Putative constructs are also sequenced and titred as described in section A.

C In Vitro Production (I)

It is possible to produce a lambda phage carrying a SASP gene solely by in vitro methods. This has been accomplished by insertion of the sspC and Cm resistance genes within the R lysis gene of lambda.

1. The lambda genome was digested with KasI, whose recognition sequence comprises a unique restriction site in lambda, occurring at base 45679, within the peptidoglycan hydrolase encoding gene, R. Digested lambda DNA was then dephosphorylated.

Figure 8:
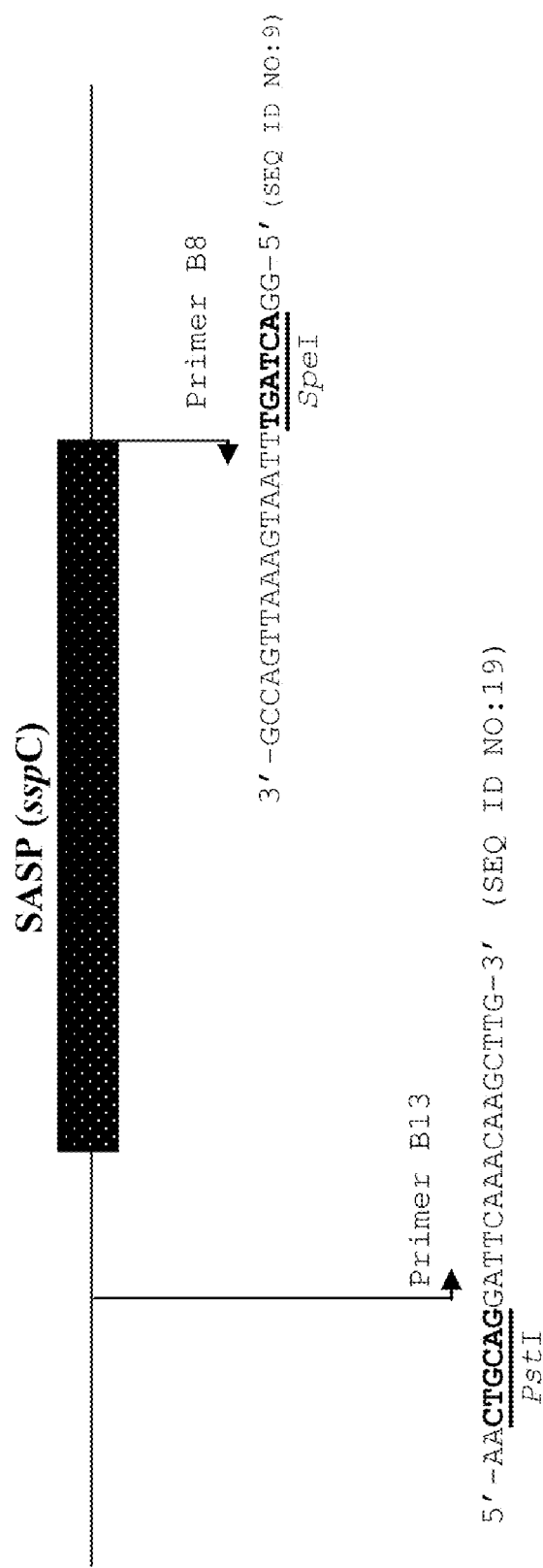
FIG. 8 shows a diagrammatic representation of part of the Bacillus subtilis genome spanning the sspC gene.

2. The sspC gene was PCR amplified with an extension time of 20 sec, using:

(i) a forward primer, B13, comprising a PstI restriction enzyme sequence (with preferred upstream bases) and sequence upstream of the sspC ribosome binding site (FIG. 8). The ribosome binding site used is that of sspC itself but could incorporate alternative sequence with the aim of potentially increasing translation (see section A 12).

Primer B13: 5'-AACTGCAGGATTCAAACAAGCTTG-3' (SEQ ID NO: 19)

ii) reverse primer B8.

Figure 9:
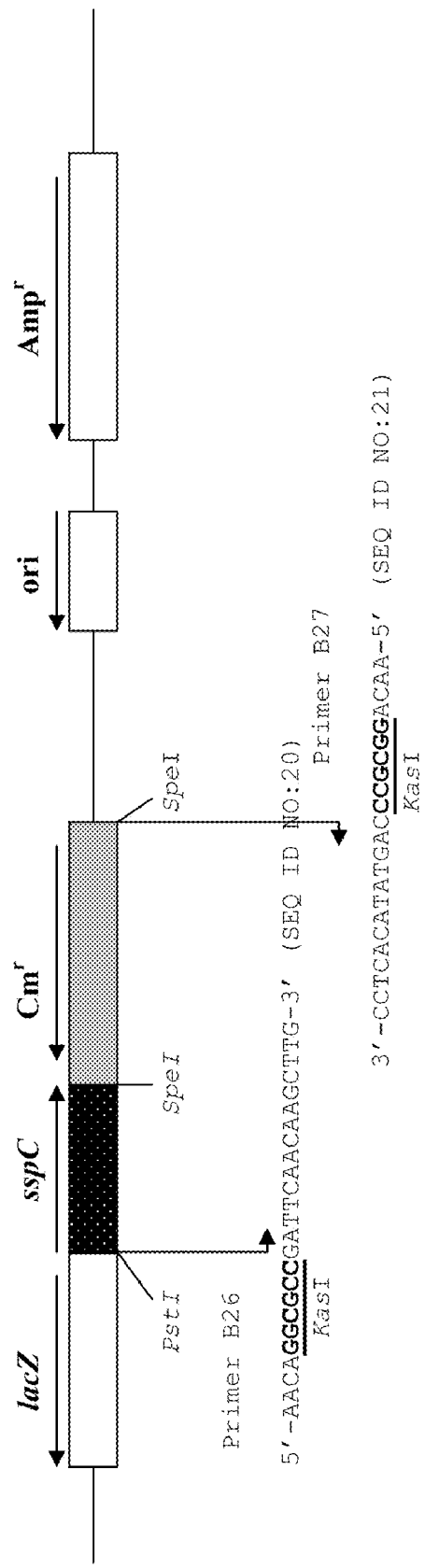
FIG. 9 shows a map of pB/PIPC.

3. The sspC PCR product was digested with PstI and SpeI and ligated to similarly digested, dephosphorylated pBluescript SK (+) to give pB/PIP. A Cm$^r$ gene (see section A 8) was inserted, in the opposite orientation, at the SpeI site at the 3' end of the sspC gene to give pB/PIPC (FIG. 9). FIG. 9 shows a linear map of pB/PIPC. The position of primers B26 and B27 is also shown.
4. The sspC/Cm fragment present in pB/PIPC was PCR amplified using:
   i) a forward primer incorporating a KasI restriction enzyme site in front of the sspC ribosome binding site sequence (see FIG. 9):

Primer B26: 5'-AACAGGCGCCGATTCAAACAAGCTTG-3' (SEQ ID NO: 20)

ii) a reverse primer incorporating a KasI restriction enzyme at the end of the Cm$^r$ gene (see FIG. 9):

Primer B27: 5'-AACAGGCGCCAGTATACACTCC-3' (SEQ ID NO: 21)

Figure 10:
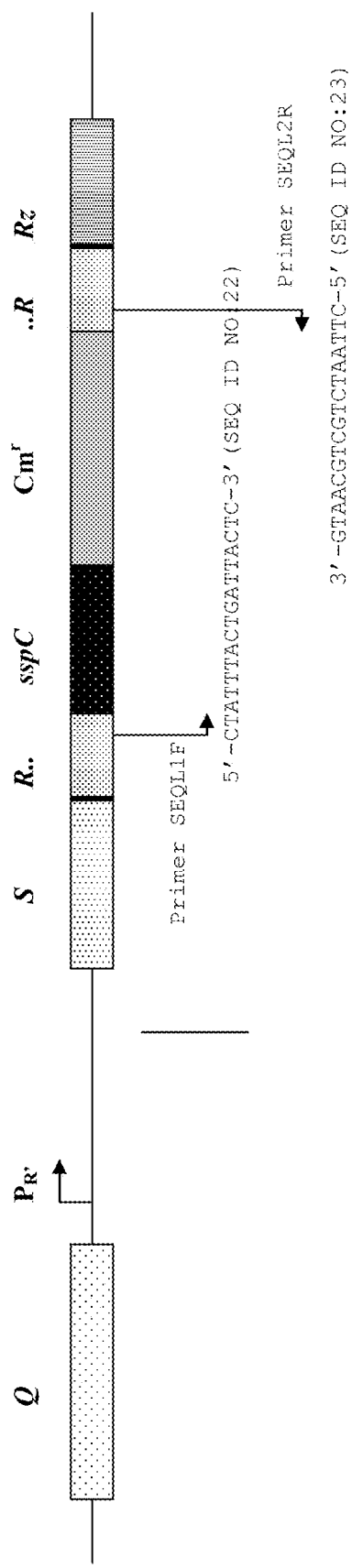
FIG. 10 shows a diagrammatic representation of a fragment comprising the RPPC-lambda construct, showing position of sequencing primers SEQL1F and SEQL2R.
Figure 11:
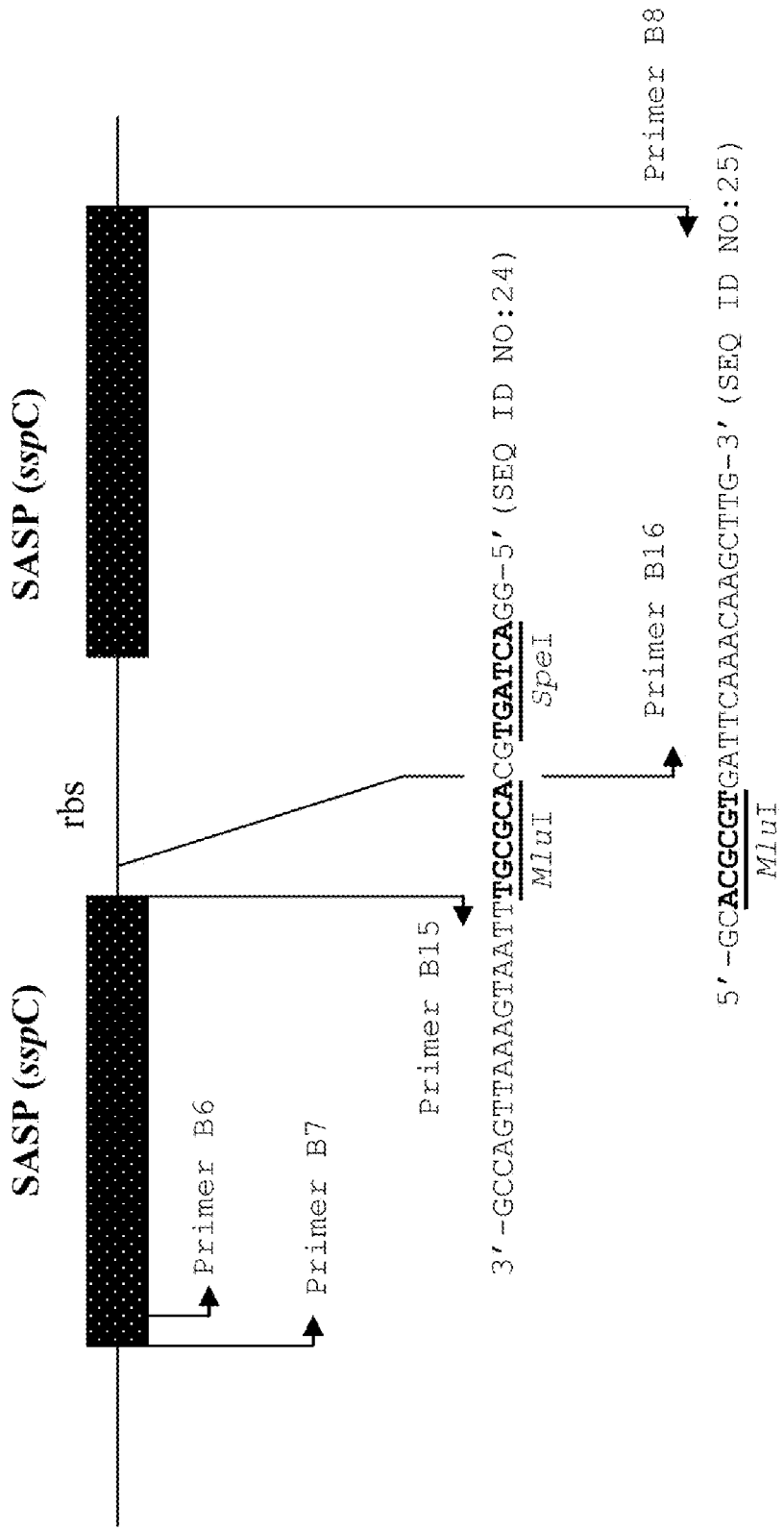
FIG. 11 shows a diagrammatic representation of tandem sspC genes and the primers used to PCR amplify the genes prior to ligation into lambda.

5. The resulting PCR product was digested with KasI and ligated into similarly digested, dephosphorylated lambda genome (see section C 1) to give SPPC-lambda (FIG. 10).
6. The recombinant lambda DNA was packaged in vitro according to method of (Hohn and Murray, 1977) or using a kit such as Packagene (Promega).
7. Serial dilutions (down to $10^{-5}$) were made of packaged lambda in phage buffer. An aliquot (100 μl) from each packaging extract dilution was added to a vial containing 0.1 ml of E. coli strain NM522, freshly grown to an OD$_{600}$ of 0.3 in LB containing 10 mM MgSO$_4$ and 0.2% maltose (w/v).
8. The preadsorption mixture was incubated at RT for 20 minutes before the mixture was pipetted in 100 μl aliquots onto the dried surface of an LB agar plate containing chloramphenicol (10 μg/ml). The plates were inverted and incubated overnight at 30° C.
9. Colonies present following overnight incubation were putative lysogens with the R lysis gene of lambda insertionally inactivated by the sspC gene. Approximately 50 colonies were transferred to two LB plates containing chloramphenicol (10 μg/ml) and the plates were incubated overnight at either 30° C. or 42° C. Colonies which grew at 30 but not at 42° C. in the presence of chloramphenicol were assumed to be lambda lysogens containing the sspC and Cm$^r$ genes. An RPPC-lambda construct was isolated and sequenced as described in section A to confirm the integrity of the sspC and Cm resistance genes and that they had integrated correctly into the lambda genome. Sequencing primers, SEQL1F from base 45613 to base 45629 (5'-CTATTTACTGATTACTC-3' (SEQ ID NO:22) and SEQL2R from base 45792 to base 45776 (5'-CTTAATCTGCTGCAATG-3' (SEQ ID NO:23) were used (see FIG. 10).

D. In Vitro/In Vivo Production Using Tandem sspC Genes

It has already been stated that protein-protein contacts are formed between α/β-type SASP while bound to DNA (Hayes and Setlow, 1998). It is possible that the formation of potential protein-protein binding surfaces induced by DNA could direct the further addition of α/β-type SASP molecules to the ends of DNA bound protein clusters, and therefore regulate protein binding (Hayes et al., 2000). The initial rate of binding of some (though not all) α/β-type SASP is second order with respect to initial unbound protein concentration, suggesting that two SASP monomers might be required for each productive binding event to occur (Hayes et al., 2000). In view of this it can be preferable to increase the level of SspC within the cell. Apart from regulating the level by means of a strong promoter or, as discussed in section A 12, a translational enhancer sequence and a concensus ribosome binding site with an optimized spacer region to enhance translation of SASP, two SASP genes can be inserted, in tandem, into the lambda genome. It is possible to achieve this using, in part, primers and methods given in previous sections.

For example to create tandem sspC genes in place of the lambda S gene, the sspC gene should be PCR amplified using primers (B6) or (B7) with a reverse primer (B15) (FIG. 11):

```
                                    (SEQ ID NO: 24)
Primer B15: 5'-GGACTAGTCGACGCGTTTAATGAAATTGACCG-3'
```

In FIG. 11, the tandem sspC genes are shown together with the primers used to PCR amplify the genes prior to ligation into inverse PCR product of pB/LF1. The product of primers B6 or B7 and B15 are ligated into inverse PCR product of pB/LF1 amplified using primers B3 and B5 or B4 and 135 (see FIG. 2). The resulting plasmids, pB/SAPB2 or pBSAPO2 respectively, are then digested with MluI and SpeI and the similarly digested PCR product of primers B16 and B8 inserted, to give either pB/SABP2T or pB/SAPO2T, respectively.

Primer B15 is similar to B8 except that it incorporates a unique restriction sequence, i.e. for MluI, between the sspC sequence and the SpeI recognition sequence. For the second sspC gene, primer B8 should be used with a forward primer (B16) that comprises the same sspC sequence as primers B13 and B23, but incorporating a restriction site that is compatible with the sspC PCR product produced from primer B15 (i.e. MluI) (FIG. 11):

```
                                    (SEQ ID NO: 25)
Primer B16: 5'-CGACGCGTGATTCAAACAAGCTTG-3'
```

Although the rbs sequence given is that of sspC itself, alternative leader sequence could be substituted to influence expression of this second sspC gene (see section A 12).

The PCR product resulting from amplification of sspC using primers B6 or B7 and B15 should be ligated with inverse PCR product of plasmid pB/LF1, amplified as described in section A. The resultant plasmid, pB/SAPB2 or pB/SAPO2, respectively should then be digested with MluI and SpeI and dephosphorylated. The PCR product resulting from amplification of sspC using primers B16 and B8 should be digested with MluI and SpeI and ligated with either of the above digested plasmids to give either plasmid pB/SAPB2T or pB/SAPO2T, respectively. Again, a $Cm^r$ gene can be inserted at the SpeI site at the end of the second sspC gene. Integration of this construct into lambda can be accomplished as described previously in section A.

Alternatively a different SASP gene, such as, SASPβ from *Clostridium bifermentans* could be inserted after the sspC gene or on its own since SASPβ has a greater DNA binding affinity than sspC, although it is less well characterised (Hayes et al., 2000).

E Examples of Effect of SASP 1. An example procedure for testing the in vitro efficacy of SASP, delivered by a bacteriophage carrying an sspC gene, to cause a reduction in viability of *E. coli* cells is as follows:

i. The *E. coli* strain to be infected is grown overnight from frozen stock or fresh agar plate in λLB (LB containing 0.2% maltose and 10 mM $MgSO_4$).

ii. This overnight culture is used to inoculate 3 ml λLB (to an $OD_{600}$ of 0.02) which is then grown at 37° C., shaking at 350 rpm until the $OD_{600}$ reaches approximately 0.3. An aliquot of this culture (1 ml) is then used directly, or 100 μl is used to make serial dilutions in 0.9 ml λLB, as appropriate so that the ratio of phage numbers to cell numbers can be varied as required.

iii. Aliquots (1 ml) of this cell culture are then transferred to a sterile Universal tube and phage lysate, or a dilution of phage lysate (made as described previously) (1 ml) is added. The cell/phage mix is incubated at 37° C., without shaking, for 30 min and then 2 ml fresh λLB is added.

iv. The $OD_{600}$ of each test sample is taken and an aliquot (100 μl) is removed, diluted in phosphate buffered saline (PBS) and 100 μl of suitable dilutions spread onto LB plates. Incubation of the samples and control is continued at 37° C. with shaking at 250 rpm and at suitable time points, for example hourly, this step is repeated.

v. Plates are incubated overnight at 37° C. and the following day, the number of colony forming units (cfu) on each plate is determined.

2. Typical results (from 4 experiments) of infecting cells by this procedure with, for example, SSPC-lambda, are given in the following table.

TABLE 1

Viability of *E. coli* cells following infection with SSPC-lambda

| Time (h) | $OD_{600}$ | cfu/ml |
|---|---|---|
| pre-infection | 0.35 | $1.4 \times 10^8$ |
| post-infection | 0.15 | $1.2 \times 10^7$ |
| 1 h post-infection | 0.13 | $5.4 \times 10^6$ |
| 2 h post-infection | 0.23 | $1.3 \times 10^6$ |
| 3 h post-infection | 0.33 | $7.0 \times 10^5$ |
| 4 h post-infection | 0.52 | $5.2 \times 10^5$ |
| 5 h post-infection | 0.58 | $3.2 \times 10^5$ |

*E. coli* cells were grown to an $OD_{600}$ of 0.35 which corresponded to approximately $1.4 \times 10^8$ cells/ml. An aliquot (1 ml) of cell culture was infected with approximately $1 \times 10^{10}$ SSPC-lambda phages (1 ml of lysate containing approximately $10^{10}$ phage/ml), as previously described, prior to addition of 2 ml fresh LB.

Figure 12:
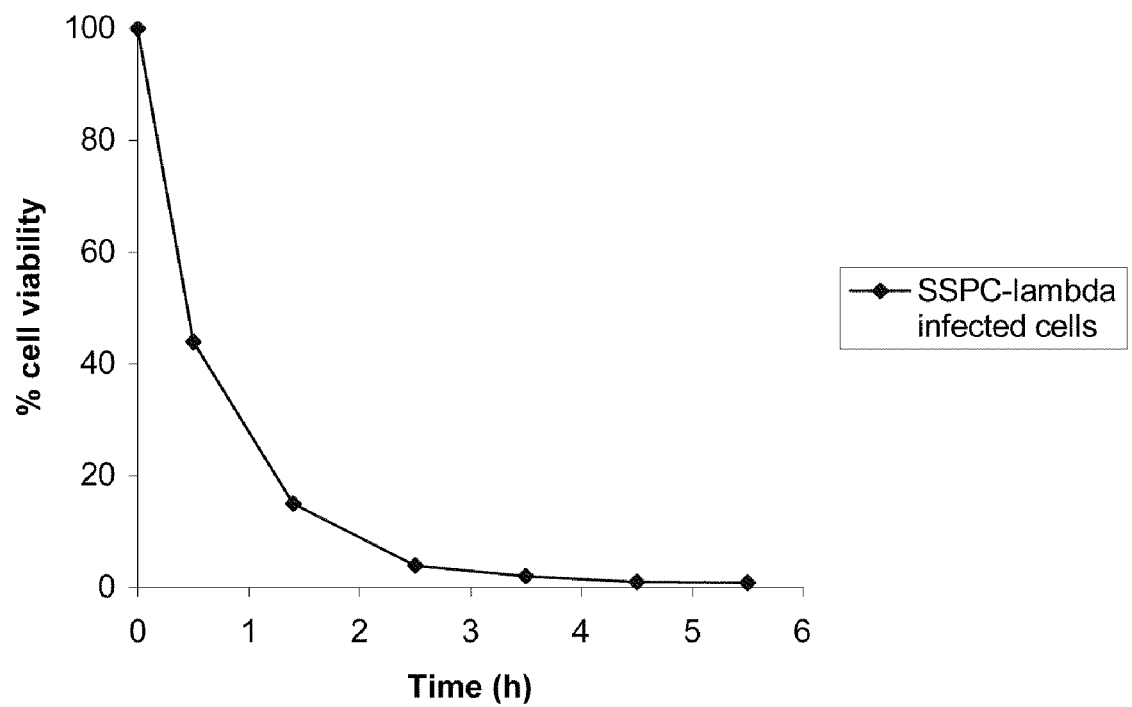
FIG. 12 shows the decrease in viability of E. coli following infection with SSPC-lambda.

From four infection experiments it has been observed that by 30 minutes post-infection of *E. coli* with SSPC-lambda there is a ≧60% drop in cell viability compared to cell numbers pre-infection; this drop in cell viability routinely increases to ≧95% by 3 hours post-infection. The decrease in cell viability taken from the experiment detailed in Table 1 is shown in FIG. 12.

3. The foregoing data can be compared to that routinely observed following production of SspC in a strain carrying an expression plasmid containing the sspC gene. Such a plasmid has been constructed, (pET/PIP) with the sspC gene inserted into the expression vector, pET24d (Novagen). In this plasmid, sspC is under the control of the T7 RNA polymerase gene promoter and production of SspC is largely repressed by the presence of 0.2% glucose in the growth medium and induced by the addition of IPTG (to 1 mM). Sequence data, obtained using standard primers T7 and B8, confirming the insertion of sspC and its integrity is given in Appendix 7. Table 2 details typical results (from 3 experiments) obtained when strain PTL14 (*E. coli* strain BL21 λDE3 containing pET/PIP) is grown as follows:

i) Strain PTL14 was grown in 25 ml LB containing Kanamycin (30 μg/ml) in a 100 ml flask at 37° C. with shaking at 250 rpm to an $OD_{600}$ of 0.25. The culture was then divided, with 12.5 ml being transferred to a fresh 100 ml flask.

ii) The culture in one of the flasks was induced by the addition of IPTG (to 1 mM) and both flasks were incubated at 37° C. with shaking at 350 rpm. Aliquots (0.5 ml) were taken from the control and sample cultures immediately pre-induction and at 30-60 min intervals thereafter for 3 hours and at 24 hours.

iii) These aliquots were used to obtain $OD_{600}$ readings and also used to make serial dilutions as appropriate in LB, and spread in 100 μl aliquots onto LB agar plates containing Kanamycin (30 μg/ml). Plates were incubated overnight at 37° C. and colony forming units (cfu) on each plate were counted and used to determine cfu per ml.

These experiments confirmed that delivery of the sspC gene to cells via a plasmid, and following expression of SspC, results in a massive reduction in cell viability. By 24 hours post-induction, viability of cells carrying the pET/PIP vector increase slightly as a result of host and/or plasmid mutations which impair SspC expression.

TABLE 2

Growth of strain PTL14 containing the sspC gene within pET24d (Novagen) in the absence (uninduced) or presence (induced) of IPTG (1 mM).

| Time (h) (post-induction) | $OD_{600}$ | | cfu/ml | |
|---|---|---|---|---|
| | Uninduced cells | Induced cells | Uninduced cells | Induced cells |
| 0 | 0.25 | 0.25 | $7.0 \times 10^7$ | $7.0 \times 10^7$ |
| 0.5 | 0.65 | 0.58 | $3.0 \times 10^8$ | $5.8 \times 10^4$ |
| 1.0 | 1.38 | 0.79 | $5.0 \times 10^9$ | $7.0 \times 10^4$ |
| 2.0 | 2.7 | 0.83 | $6.0 \times 10^{11}$ | $6.0 \times 10^3$ |
| 3.0 | 3.58 | 1.20 | $9.8 \times 10^{11}$ | $3.0 \times 10^3$ |
| 24 | 4.23 | 1.52 | $8.0 \times 10^{11}$ | $6.6 \times 10^7$ |

Figure 13:
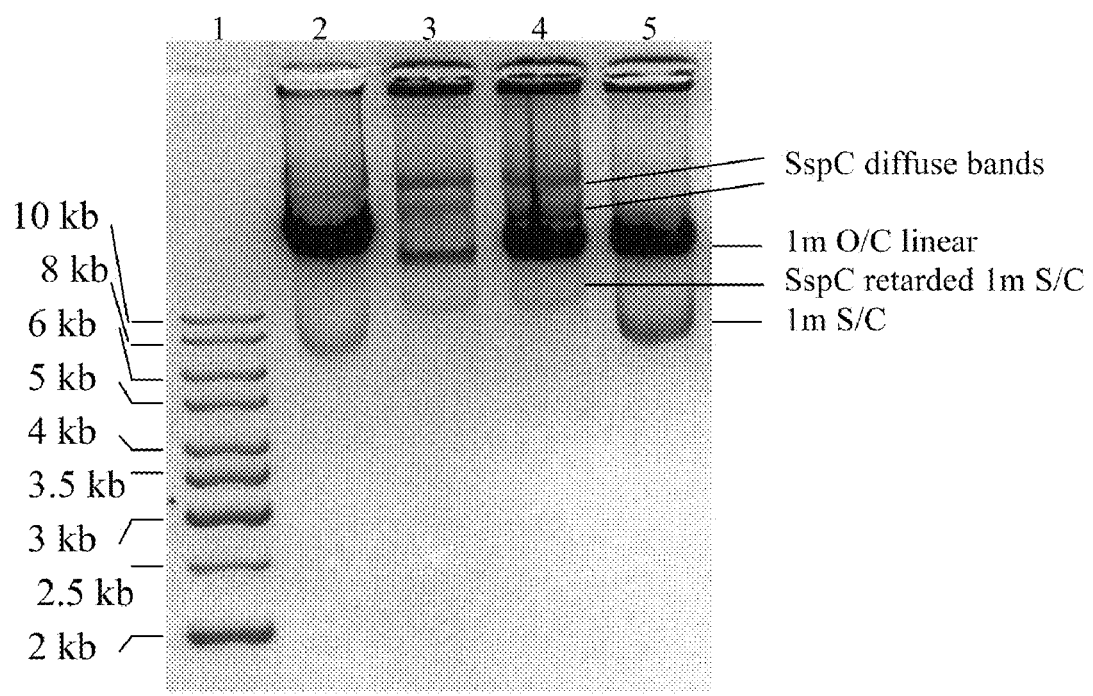
FIG. 13 shows a gel demonstrating the banding patterns of plasmid DNA prepared from strains grown +/−production of SspC.

The observed reduction of cell viability in cells expressing sspC is supported by data obtained following isolation of plasmid DNA from strain PTL14 grown and induced or repressed as detailed above. As a negative control, *E. coli* strain NM522 was also transformed with plasmid pET/PIP (to give strain PTL38) since NM522 does not contain the T7 RNA polymerase promoter and thus no expression of sspC can occur. Plasmid DNA from strain PTL14 (induced and uninduced) and strain PTL38, grown in parallel, was isolated according to the protocol of Kieser (1984). In order to relax plasmid supercoiling, plasmid DNA from each sample (0.5-1 μg) was incubated with Topoisomerase I (2 Units) for 2 h at 37° C. The DNA was then resolved by TAE agarose gel electrophoresis (5 h at 4.5 V/cm) in the presence of 0.06 μg/ml ethidium bromide (Keller, 1975). Following visualization by UV transillumination the gel was photographed as shown in FIG. 13, which shows banding patterns of plasmid DNA prepared from strains grown±production of SspC. The lanes are as follows Lane 1 1 kb DNA ladder (0.25 μg total DNA)
Lane 2 Uninduced pET/PIP in *E. coli* strain BL21 ☐DE3 (PTL14)
Lane 3 Induced Pet/Pip in *E. Coli* Strain BL21 ☐DE3 (PTL14)
Lane 4 Induced Pet/Pip in *E. Coli.* Strain BL21 ☐DE3 (PTL14) duplicate prep
Lane 5 Uninduced pET/PIP in *E. coli* strain NM522 (PTL38)

By comparison with pET/PIP DNA prepared from strain PTL38, there is a clear change in the plasmid DNA forms in the presence of SspC which is more markedly pronounced under conditions of induction (lanes 3 and 4). A much less marked alteration in profile is also present under conditions of leaky T7 RNA polymerase expression in the uninduced sample (lane 2). The chief profile changes associated with the high level of SspC expression are:
  i) Retardation of the monomer supercoiled form (1 m S/C) (lanes 3 and 4) relative to the uninduced strain BL21 (lane 2) and strain PTL38 (lane 5).
  ii) Generation of diffuse bands running behind the monomer linear/open circular form (lanes 3 and 4).

The retardation of the monomeric supercoiled plasmid pET/PIP form when T7 RNA polymerase expression is induced (lanes 3 and 4) and, in particular, the diffuse bands in lanes 3 and 4 are characteristic of DNA protein complexes.

The absence of these bands in plasmid DNA from uninduced cells (lane 5) is consistent with the retardation and diffuse bands being formed by complexes between pET/PIP DNA and SspC protein.

These data indicate that SspC expressed from a plasmid form can also be regarded as having potential application in pesticide or GM plant applications.

4. To demonstrate the importance of level of expression of sspC, a lambda phage has been constructed with the sspC gene inserted within the S gene but utilising the T7 RNA polymerase ribosome binding site. This strain (ST7PC) was constructed in an identical way to SPPC-Lambda except the T7 rbs is substituted for the native sspC rbs. Following the protocol used for SSPC-lambda infection, infecting cells with ST7PC-lambda results in a temporally accelerated loss of viability. For example, in a typical experiment, a $\geq 95\%$ reduction in cell viability is seen by 1 hour post infection, with a $\geq 99\%$ reduction within 3 h (see Table 3). These results indicate that utilizing an alternative rbs provide a means to modulate expression levels of SspC.

TABLE 3

Viability of cells following infection with ST7PC-lambda

| Time (h) | OD$_{600}$ | cfu/ml |
|---|---|---|
| pre-infection | 0.39 | $3.2 \times 10^8$ |
| post-infection | 0.15 | $3.5 \times 10^7$ |
| 1 h post-infection | 0.18 | $3.7 \times 10^6$ |
| 2 h post-infection | 0.37 | $3.0 \times 10^6$ |
| 3 h post-infection | 0.34 | $7.2 \times 10^5$ |
| 4 h post-infection | 0.45 | $6.8 \times 10^5$ |
| 5 h post-infection | 0.47 | $6.2 \times 10^5$ |

APPENDIX 1

A list of all the α/β type SASP which have been sequenced to date together with their related protein sequences

*Bacillus subtilis*

```
SASP A   mannnsgnsn nllvpgaaqa idqmkleias efgvnlgadt tsrangsvgg eitkrlvsfa qqnmgggqf      (SEQ ID NO: 26)
SASP B   manqnssndl lvpgaaqaid qmkleiasef gvnlgadtts rangsvggei tkrlvsfaqq qmggrvq        (SEQ ID NO: 27)
SASP C   maqqsrsrsn nnndllipqa asaieqmkle iasefgvqlg aettsrangs vggeitkrlvr laqqnmggq fh (SEQ ID NO: 28)
SASP D   masrnklvvp gveqaldqfk levaqefgvn lgsdtvaran gsvggemtkr lvqqaqsqln gttk           (SEQ ID NO: 29)
```

*Bacillus megaterium*

```
SASP A   mantnklvap gsaaaidqmk yeiasefgvn lgpeataran gsvggeitkr lvqmaeqqlg gk             (SEQ ID NO: 30)
SASP C   manyqnasnr nssnklvapg aqaaidqmkf eiasefgvnl gpdatarang svggeitkrl vqlaeqnlgg    (SEQ ID NO: 31)
         ky
SASP C1  mannnssnnn ellvygaeqa idqmkyeias efgvnlgadt tarangsvgg eitkrlvqla eqqlgggrf      (SEQ ID NO: 32)
SASP C2  mannkssnnn ellvygaeqa idqmkyeias efgvnlgadt tarangsvgg eitkrlvqla eqqlgggrsk     (SEQ ID NO: 33)
         ttl
SASP C3  martnklltp gveqfldqyk yeiaqefgvt lgsdtaarsn gsvggeitkr lvqqaqahls gstqk          (SEQ ID NO: 34)
SASP C4  mannkssnnn ellvygaeqa idqmkyeias efgvnlgadt tarangsvgg eitkrlvqla eqqlgggrf      (SEQ ID NO: 35)
SASP C5  mansrnkssn elavhgaqqa idqmkyeias efgvtlgpdt tarangsvgg eitkrlvqma eqqlgggrsk     (SEQ ID NO: 36)
         sls
SASP C-1 mannnssnnn ellvygaeqa idqmkyeias efgvnlgadt tarangsvgg eitkrlvqla eqlgggrf       (SEQ ID NO: 37)
SASP C-2 mannkssnnn ellvygaeqa idqmkyeias efgvnlgadt tarangsvgg eitkrlvqla eqlgggrskt     (SEQ ID NO: 38)
         tl
```

*Bacillus cereus*

```
SASP 1   mgknnsgsrn evlvrgaeqa ldqmkyeiaq efgvqlgadt tarsngsvgg eitkrlvama eqqlggranr     (SEQ ID NO: 39)
SASP 2   msrstnklav pgaesaldqm kyeiaqefgv qlgadatara ngsvggeitk rlvslaeqql ggyqk          (SEQ ID NO: 40)
SASP C5  mlfiniqrye sdtneilisa ttstieqmky eiafelgvtl gpdtshhlqm vriggeitkr lvrmaekqlt     (SEQ ID NO: 41)
         gqyrlh
```

*Bacillus stearothermophilus*

```
SASP 1   mpnqsgsnss nqllvpgaaq vidqmkfeia sefgvnlgae ttsrangsvg geitkrlvsf aqqqmgggvq     (SEQ ID NO: 42)
```

*Bacillus firmus*

```
SASP A   mannnssnql vvpgvqqald qmkyeiasef gvqlgpdata rangsvggei tkrlvqmaeq qmggyqk        (SEQ ID NO: 43)
```

APPENDIX 1-continued

A list of all the α/β type SASP which have been sequenced
to date together with their related protein sequences

*Clostridium bifermentans*

```
SASP α   ttnnnnntkav peakaalkqm kielanelgi snydtadkgn mtarqngyvg gymtkklvem aeqqmsgqqr    (SEQ ID NO: 44)
SASP β   stkkavpeak aalnqmklei anelglsnye svdkgnltar qngyvggymt kklvemaerq msgk           (SEQ ID NO: 45)
```

*Clostridium perfringens*

```
SASP 1   mskslvpeak nglskfknev arelgvpfsd yngdlssrqc gsvggemvkr mveayesqik                (SEQ ID NO: 46)
SASP C1  msqhlvpeak nglskfknev aaemgvpfsd yngdlsskqc gsvggemvkr mveqyekgi                 (SEQ ID NO: 47)
SASP C2  msqhlvpeak nglskfknev anemgvpfsd yngdlssrqc gsvggemvkr mvekyeqsmk                (SEQ ID NO: 48)
```

*Sporosarcina halophila*

```
SASP 1   mannnssnel vvpgvqqald qmkyeiaqef gvqlgadsts rangsvggei tkrlvqmaeq qfggqqygqq     (SEQ ID NO: 49)
         qk
```

*Sporocarcina ureae*

```
SASP 1   mtnnnnsnsn qllvpgvqqa inqmkeeian efgvnlgpds tsrangsvgg eitkrlvrqa qsqmngytk      (SEQ ID NO: 50)
SASP 2   mpnnnssnql lvpgvqqaln qmkeeiasef gvqlgpdass rangsvggei tkrlvrqaqs qmngytk       (SEQ ID NO: 51)
```

Thermoactinomyces thalpophilus
```
SASP 1   maqqgrnrss nqllvagaaq aidqmkfeia qefgvtlgad ttsrangsvg geitkrlvsl aqqqlgggts f   (SEQ ID NO: 52)
```

APPENDIX 2

An alignment of α/β type SASP protein sequences known to date.

```
SASP A   (1)       mannnsgnsnnllvpgaaqaidqmkleiasefgvnlgadttsrangsvggeitkrlvsfaqqnmgggqf
                   (SEQ ID NO: 26)
SASP B   (1)       manqnssndllvpgaaqaidqmkleiasefgvnlgadttsrangsvggeitkrlvsfaqqqmggrvq
                   (SEQ ID NO: 27)
SASP C   (1)       maqqsrsrsnnnndllipqaasaieqmkleiasefgvqlgaettsrangsvggeitkrlvrlaqqnmgggqfh
                   (SEQ ID NO: 28)
SASP D   (1)            masrnklvvpgveqaldqfklevaqefgvnlgsdtvarangsvggemtkrlvqqaqsqlngttk
                   (SEQ ID NO: 29)
SASP A   (2)           mantnklvapgsaaaidqmkyeiasefgvnlgpeatarangsvggeitkrlvqmaeqqlggk
                   (SEQ ID NO: 30)
SASP C   (2) manyqnasnrnssnklvapgaqaaidqmkfeiasefgvnlgpdatarangsvggeitkrlvqlaeqnlggky
                   (SEQ ID NO: 31)
SASP C1  (2)          mannnssnnnellvygaeqaidqmkyeiasefgvnlgadttarangsvggeitkrlvqlaeqqlgggrf
                   (SEQ ID NO: 32)
SASP C2  (2)          mannkssnnnellvygaeqaidqmkyeiasefgvnlgadttarangsvggeitkrlvqlaeqqlgggrskttl
                   (SEQ ID NO: 33)
SASP C3  (2)           martnklltpgveqfldqykyeiaqefgvtlgsdtaarsngsvggeitkrlvqqaqahlsgstqk
                   (SEQ ID NO: 34)
SASP C4  (2)          mannkssnnnellvygaeqaidqmkyeiasefgvnlgadttarangsvggeitkrlvqlaeqqlgggrf
                   (SEQ ID NO: 35)
SASP C5  (2)          mansrnkssnelavhgaqqaidqmkyeiasefgvtlgpdttarangsvggeitkrlvqmaeqqlgggrsksls
                   (SEQ ID NO: 36)
SASP C-1 (2)          mannnssnnnellvygaeqaidqmkyeiasefgvnlgadttarangsvggeitkrlvqlaeqlgggrf
                   (SEQ ID NO: 37)
SASP C-2 (2)          mannkssnnnellvygaeqaidqmkyeiasefgvnlgadttarangsvggeitkrlvqlaeqlgggrskttl
                   (SEQ ID NO: 38)
SASP 1   (3)          mgknnsgsrnevlvrgaeqaldqmkyeiaqefgvqlgadttarsngsvggeitkrlvamaeqqlggranr
                   (SEQ ID NO: 39)
SASP 2   (3)           msrstnklavpgaesaldqmkyeiaqefgvqlgadatarangsvggeitkrlvslaeqqlggyqk
                   (SEQ ID NO: 40)
SASP 1   (4)          mpnqsgsnssnqllvpgaaqvidqmkfeiasefgvnlgaettsrangsvggeitkrlvsfaqqqmgggvq
                   (SEQ ID NO: 42)
SASP A   (5)          mannnssnqlvvpgvqqaldqmkyeiasefgvqlgpdatarangsvggeitkrlvqmaeqqmggyqk
                   (SEQ ID NO: 43)
SASP 1   (6)          mannnssnelvvpgxrqqaldqmkyeiaqefgvqlgadstsrangsvggeitkrlvqmaeqqfggqqygqqqk
                   (SEQ ID NO: 49)
SASP 1   (7)          mtnnnnsnsnqllvpgvqqainqmkeeianefgvnlgpdstsrangsvggeitkrlvrqaqsqmngytk
                   (SEQ ID NO: 50)
SASP 2   (7)          mpnnnssnqllvpgvqqalnqmkeeiasefgvqlgpdassrangsvggeitkrlvrqaqsqinngytk
                   (SEQ ID NO: 51)
SASP 1   (8)          maqqgrnrssnqllvagaaqaidqmkfeiaqefgvtlgadttsrangsvggeitkrlvslaqqqlgggtsf
                   (SEQ ID NO: 52)
                              *         * * * **** **      * ****** ***** *     *

SASP α   (9) ttnnnntkavpeakaalkqmkleianelgisnydtadkgnmtarqngyvggymtkklvemaeqqmsgqqr
                   (SEQ ID NO: 44)
```

APPENDIX 2-continued

An alignment of α/β type SASP protein sequences known to date.

```
SASP β    (9)   stkkavpeakaalnqmkleianelglsnyesvdkgnltarqngyvggymtkklvemaerqmsgk
                (SEQ ID NO: 45)
SASP 1    (10)  mskslvpeakng1skfknevarelgvpfsdyngd--lssrqcgsvggemvkrmveayesqik
                (SEQ ID NO: 46)
SASP C1   (10)  msqhlvpeakng1skfknevaaemgvpfsdyngd--lsskqcgsvggemvkrmveqyekgi
                (SEQ ID NO: 47)
SASP C2   (10)  msqhlvpeakng1skfknevanemgvpfsdyngd--lssrqcgsvggemvkrmvekyeqsmk
                (SEQ ID NO: 48)
                ◊◊◊◊◊◊  ◊    * * * * *          ◊ * *** ◊ *  * ◊  ◊
```

◊ Residues conserved in Clostridia SASP
Key
(1) *Bacillus subtilis*
(2) *Bacillus megaterium*
(3) *Bacillus cereus*
(4) *Bacillus stearothermophilus*
(5) *Bacillus firmus*
(6) *Sporosarcina halophila*
(7) *Sporocarcina ureae*
(8) *Thermoactinomyces thalpophilus*
* Residues conserved in *Bacillus* and *Sporosarcina* SASP as well as the *Thermoactinomyces* SASP.
(9) *Clostridium biferrnentans*
(10) *Clostridium perfringens*
* Residues conserved in *Bacillus*, *Sporosarcina* and *Clostridia* SASP as well as the *Thermoactinomyces* SASP.

APPENDIX 3

DNA sequence of sspc encoding SASP C from *Bacillus subtilis* strain 168 (obtained from Subtilist at the Institut Pasteur)

(SEQ ID NO: 53)

```
atggctcaac aaagtagatc aagatcaaac aacaataatg atttactaat     50
tcctcaagca gcttcagcta ttgaacaaat gaaacttgaa atagcttctg    100
agtttggtgt tcaattaggc gctgagacta catctcgtgc aaacggttca    150
gttggtggag aaatcactaa acgtttagtt cgcttagctc aacaaaacat    200
gggcggtcaa tttcattaat ttatgagggg gataattccc ctctcttttt    250
taagtcttct ctaaatccat ac                                  272
```

Note:
The sspC gene extends from 1-219 (inclusive)
The terminator sequence extends from 225-243 (inclusive)

APPENDIX 4

A list of common pathogens and some of their phages. (This list is representative but not exhaustive).

Coliphages:

Bacteriophage lambda
Bacteriophage 933W (*Escherichia coli* O157:H7)
Bacteriophage VT2-Sa (*E. coli* O157:H7)
Coliphage 186
Coliphage P1
Coliphage P2
Coliphage N15
Bacteriophage T3
Bacteriophage T4
Bacteriophage T7
Bacteriophage KU1
Bacteriophages of *Salmonella* spp Bacteriophage Felix
Bacteriophage P22
Bacteriophage L
Bacteriophage 102
Bacteriophage 31
Bacteriophage F0
Bacteriophage 14

APPENDIX 4-continued

A list of common pathogens and some of their phages. (This list is representative but not exhaustive).

Bacteriophage 163
Bacteriophage 175
Bacteriophage Vir
Bacteriophage ViVI
Bacteriophage 8
Bacteriophage 23
Bacteriophage 25
Bacteriophage 46
Bacteriophage E15
Bacteriophage E34
Bacteriophage 9B
Bacteriophages of *Shigella dysenteriae*

Bacteriophage ϕ80
Bacteriophage P2
Bacteriophage 2
Bacteriophage 37
Bacteriophages of *Vibrio cholerae*

Bacteriophage fs-2
Bacteriophage 138
Bacteriophage 145

APPENDIX 4-continued

A list of common pathogens and some of their phages.
(This list is representative but not exhaustive).

Bacteriophage 149
Bacteriophage 163
Bacteriophages of *Mycoplasma arthritidis*

Bacteriophage MAV1
Bacteriophages of *Streptococci*

Bacteriophage CP-1
Bacteriophage φXz40
Bacteriophage 1A
Bacteriophage 1B
Bacteriophage 12/12
Bacteriophage 113
Bacteriophage 120
Bacteriophage 124
Bacteriophages of *Pseudomonas aeruginosa*

Bacteriophage D3
Bacteriophage φCTX
Bacteriophage PP7
Bacteriophages of *Haemophilus influenzae*

Bacteriophage S2
Bacteriophage HP1
Bacteriophage flu
Bacteriophage Mu
Bacteriophages of *Staphylococcus aureus*

Bacteriophage Twort
Bacteriophage tIII-29S
Bacteriophage φPVL
Bacteriophage φPV83
Bacteriophage φ11
Bacteriophage φ12
Bacteriophage φ13
Bacteriophage φ42
Bacteriophage φ812
Bacteriophage K
Bacteriophage P3
Bacteriophage P14
Bacteriophage UC18
Bacteriophage 15
Bacteriophage 17
Bacteriophage 29

Bacteriophage 42d
Bacteriophage 47
Bacteriophage 52
Bacteriophage 53
Bacteriophage 79
Bacteriophage 80
Bacteriophage 81
Bacteriophage 83
Bacteriophage 85
Bacteriophage 93
Bacteriophage 95
Bacteriophage 187
Bacteriophages of Chlamydia Bacteriophage φCPAR39
Mycobacteriophage Bacteriophage L5
Bacteriophage LG
Bacteriophage D29
Bacteriophage Rv1
Bacteriophage Rv2
Bacteriophage DSGA
Bacteriophages of *Listeria monocytogenes*

Bacteriophage A118
Bacteriophage 243
Bacteriophage A500
Bacteriophage A511
Bacteriophage 10
Bacteriophage 2685
Bacteriophage 12029
Bacteriophage 52
Bacteriophage 3274
Bacteriophages of *Klebsiella pneumoniae*

Bacteriophage 60
Bacteriophage 92
Bacteriophages of *Yersinia pestis*

Bacteriophage R
Bacteriophage Y
Bacteriophage P1

APPENDIX 5

A list of bacteriophage receptors and ligands from bacteria and other cells. (This list is representative but not exhaustive).

| Receptor/ligand | Phage |
|---|---|
| Porins (OmpA, OmpC and LamB etc.) (e.g. proteins involved in transport of specific substrates: phosphates, nucleosides, iron, vitamin B12, maltose and maltodextrins) | Lambda and other coliphages such as T-Even coliphage Ox2, Host range mutant of Ox2 coliphage |
| Peptidoglycan | Phage A25 (Group A Streptococci) *Listeria monocytogenes* phage Coliphage T5 |
| N-acetylglucosamine and rhamnose substituents of teichoic acids | *Listeria monocytogenes* Phage |
| L-rhamnose | Phage PL-1 (*Lactobacillus casei*) |
| Exopolysaccharides and Lipopolysaccharides | Siphovirus Phage NM8 (*Rhizobium meliloti*) Host range mutant of Ox2 coliphage |
| Teichoic acid | Phages SP 50 and φ25 (*Bacillus subtilis*) |

APPENDIX 5-continued

A list of bacteriophage receptors and ligands from bacteria and other cells. (This list is representative but not exhaustive).

| Phage |
|---|

Modified receptor/ligand affinities

| | |
|---|---|
| Fibroblast growth factor receptor | Phage M13 displaying FGF2 on coats |
| Epidermal growth factor receptor | Phage M13 displaying EGF on coats |

APPENDIX 6

Sequence data from SSPC-LAMBDA (positive strand only), obtained using primers:
13F1 and b30 (see Figure 7, Section A 11):

(SEQ ID NO: 54)

Front end of λ fragment originating from pB/IPSAPOC (base 44660)

CTAGTTGGTCACTTCGACGTATCGTCTGGAACTCCAACCATCGCAGGCAGAGAGGTCTGCAAAATGCAAT
CCCGAAACAGTTCGCAGGTAATAGTTAGAGCCTGCATAACGGTTTCGGGATTTTTTATATCTGCACAACA
GGTAAGAGCATTGAGTCGATAATCGTGAAGAGTCGGCGAGCCTGGTTAGCCAGTGCTCTTTCCGTTGTGC
TGAATTAAGCGAATACCGGAAGCAGAACCGGATCACCAAATGCGTACAGGCGTCATCGCCGCCCAGCAAC
AGCACAACCCAAACTGAGCCGTAGCCACTGTCTGTCCTGAATTCATTAGTAATAGTTACGCTGCGGCCTT
TTACACATGACCTTCGTGAAAGCGGGTGGCAGGAGGTCGCGCTAACAACCTCCTGCCGTTTTGCCCGTGC
ATATCGGTCACGAACAAATCTGATTACTAAACACAGTAGCCTGGATTTGTTCTATCAGTAARCGACCTTA
TTCCTAATTAAATAGAGCAAATCCCCTTATTGGGGGTAAGA

Start of sspC gene

CATGACCATGGCTCACCAAAGTAGATCAAGATCAAACAACAATAATGATTTACTAATTC
    NcoI
CTCAAGCAGCTTCAGCTATTGAACAAATGAAACTTGAAATAGCTTCTGAGTTTGGTGTTCAATTAGGCGC
TGAGACTACATCTCGTGCAAACGGTTCAGTTGGTGGAGAAATCACTAA

End of sspC gene    End of
ACGTTTAGTTCGCTTAGCTCAACAAAACATGGGCGGTCAATTTCATTAAACTAGTGCAC Cm^r gene fragment                                      SpeI

CAATAACTGCCTTAAAAAAATTACGCCCCGCCCTGCCACTCATCGCAGTACTGTTG

B54 and B55:

(SEQ ID NO: 55)

TGTTCAGCTACTGACGGGGTGGTGCGTAACGGCAAAAGCACCGCCGGACATCAGCGCTA
    Start of Cm^r gene
    fragment            λ base 45499

GCGGAGTGTATACTGGACTAGTGAAATCAATAATCAACGTAAGGCGTTCCTCGATATGC

TGGCGTGGTCGGAGGGAACTGATAACGGACGTCAGAAAACCAGAAATCATGGTTATGACGTCATTGTAGG
CGGAGAGCTATTTACTGATTACTCCGATCACCCTCGCAAACTTGTCACGCTAAACCCAAAACTCAAATCA
ACAGGCGCCGGACGCTACCAGCTTCTTTCCCGTTGGTGGGATGCCTACCGCAAGCAGCTTGGCCTGAAAG
ACTTCTCTCCGAAAAGTCAGGACGCTGTGGCATTGCAGCAGATTAAGGAGCGTGGCGCTTTACCTATGAT
TGATCGTGGTGATATCCGTCAGGCAATCGACCGTTGCAGCAATATCTGGGCTTCACTGCCGGCGCTGGT
TATGGTCAGTTCGAGCATAAGGCTGACAGCCTGATTGCAAAATTCAAAGAAGCGGGCGGAACG

Ενδοφλ fragment originating from pB/IPSAPOC (base 45972)

GTCAGAGAGATTGATGTATGAGCAGAGTCACCGCG

APPENDIX 7

Sequence data from pET/PIP (positive strand only), obtained using primers:
T3 and B8

(SEQ ID NO: 56)

```
        T7 promoter
CTCGATCCCGCGAAATTAATACGACTCACTATAGGGGAATTGTGAGCGGATAACAATTC T7 rbs        Start of sspC gene
CCCTCTAGAAATAATTTTGTTTAACTTTAAGAAGGAGATATACCATGGCTCAACAAAGT
                                              NcoI
AGATCAAGATCAAACAACAATAATGATTTACTAATTCCTCAAGCAGCTTCAGCTATTGAACA
AATGAAACTTGAAATAGCTTCTGAGTTTGGTGTTCAATTAGGCGCTGAGACTACATCTCGTG
CAAACGGTTCAGTTGGTGGAGAAATCACTAAACGTTTAGTTCGCTTAGCTCAA
            End of sspC ORF
CAAAACATGGGCGGTCAATTTCATTAATTTATGAGGGGATAATTCCCCTCTCTTTTTT
End of sspC termination sequence
AAGTCTTCTCTAAATCCATACCTCGAGCACCACCACCACCACCACTGA
                    XhoI
```

REFERENCES

Cao, J., Y. Sun, T. Berlindh, B. Mellgard, Z. Li, B. Mardh and S. Mardh. 2000. *Biochim. Biophys. Acta.* 1474:107-113.

Donnellan, J. E. jnr. and R. B. Setlow, 1965. *Science.* 149: 308-310

Fairhead, H. and P. Setlow. 1991. *J. Bacteriol.* 174:2874-2880

Fairhead, H., B. Setlow and P. Setlow. 1993. *J. Bacteriol.* 175:1367-1374.

Hawes Hackett, R. and P. Setlow. 1987. *J. Bacteriol.* 169: 1985-1992.

Hayes, C. S., Z-Y. Peng and P. Setlow. 2000. *J. Biol. Chem.* In press.

Kassner, P. D., A. A. Burg, A. Baird and D. Larocca. 1999. *Biochem. Biophys. Res. Commun.* 264:921-928.

Keller, W. 1975. Determination of the number of superhelical turns in simian virus 40 DNA by gel electrophoresis. *Proc. Nat. Acad. Sci. USA.* 72:4876-4880.

Kieser, T. 1984. Factors affecting the isolation of CCC-DNA from *Streptomyces lividans* and *E. coli*. *Plasmid* 12:19-36.

Larocca, D., A. Witte, W. Johnson, C. G. Pierce and A. Baird. 1998. *Hum. Gene Ther.* 9:2393-2399.

Larocca, D., P. Kassner, A. Witte, R. Ladner, G. F. Pierce and A. Baird. 1999. *FASEB J.* 13:727-734.

Mohr, S. C., N. V. H. A. Sokolov, C. He and Peter Setlow. 1991. *Proc. Natl. Acad. Sci. USA* 88: 77-81.

Nicholson, W. L., and P. Setlow, 1990. J. Bacteriol. 172:7-

Nicholson, W. L., B. Setlow and P. Setlow. 1990a. *J. Bacteriol.* 172:6900-6906.

Nicholson, W. L., B. Setlow and P. Setlow. 1990b. *J. Bacteriol.* 173:1642-1653

Nicholson, W. L., B. Setlow and P. Setlow. 1991. *Proc. Natl. Acad. Sci. USA* 88: 8288-8292.

Pohle, W. and H. Fritzche. 1980. *Nucleic Acids Res.* 8:2527-2535.

Poul, M. and J. D. Marks. 1999. *J. Mol. Biol.* 288:203-211

Sambrook, J., E. F. Fritsch, T. Maniatis, 1989. In Molecular Cloning: A Laboratory Manual, CSHL Press Setlow, B., A. R. Hand and P. Setlow. 1991. *J. Bacteriol.* 173:1642-1653.

Setlow, B., D. Sun and P. Setlow. 1992. *J. Bacteriol.* 174: 2312-2322.

Setlow, P. 1988. *Ann. Rev. Mcrobiol.* 42:319-338.

de Vries, G. E., C. K. Raymond and R. A. Ludwig. 1984 *Proc. Natl. Acad. Sci. USA* 81:6080-6084.

The invention claimed is:

1. A composition for treating or inhibiting a bacterial infection comprising a polynucleotide encoding an α/β type small acid-soluble spore protein (SASP) in a bacteriophage delivery system which targets a bacterial cell.

2. A composition according to claim 1, wherein the polynucleotide is incorporated in the genome of the bacteriophage.

3. A composition according to claim 1, wherein the bacteriophage is a non-lysogenic bacteriophage.

4. A composition according to claim 1, wherein the bacteriophage has been modified to increase or alter its host specificity.

5. A composition for inhibiting or preventing bacterial growth comprising a polynucleotide encoding an α/β type small acid-soluble spore protein (SASP) in a bacteriophage delivery system which targets a bacterial cell.

6. A composition according to claim 5, wherein the polynucleotide is incorporated in the genome of the bacteriophage.

7. A composition according to claim 5, wherein the bacteriophage is a non-lysogenic bacteriophage.

8. A composition according to claim 5, wherein the bacteriophage has been modified to increase or alter its host specificity.

9. A composition for treating or inhibiting a bacterial infection comprising a polynucleotide encoding an α/β type small acid-soluble spore protein (SASP) in a bacteriophage which targets a bacterial cell, wherein the protein comprises the amino acid sequences kxexaxexg and gxvggxxxk, where x is any amino acid.

10. A composition for inhibiting bacterial cell growth comprising a polynucleotide encoding an α/β type small acid-soluble spore protein (SASP) in a bacteriophage which targets a bacterial cell, wherein the protein comprises the amino acid sequences kxexaxexg and gxvggxxxk, where x is any amino acid.

* * * * *

SEQUENCE LISTING

```
<160> NUMBER OF SEQ ID NOS: 60

<210> SEQ ID NO 1
<211> LENGTH: 69
<212> TYPE: PRT
<213> ORGANISM: Artificial Sequence
<220> FEATURE:
<223> OTHER INFORMATION: Description of Artificial Sequence:
      Illustrative small acid-soluble protein (SASP)

<400> SEQUENCE: 1

Met Ala Asn Asn Asn Ser Ser Asn Ser Asn Glu Leu Leu Val Pro Gly
 1               5                  10                  15

Ala Glu Gln Ala Ile Asp Gln Met Lys Tyr Glu Ile Ala Ser Glu Phe
            20                  25                  30
```

```
Gly Val Asn Leu Gly Ala Asp Thr Thr Ala Arg Ala Asn Gly Ser Val
        35                   40                  45

Gly Gly Glu Ile Thr Lys Arg Leu Val Gln Leu Ala Glu Gln Gln Leu
    50                  55                  60

Gly Gly Gly Thr Lys
 65
```

```
<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
aactgcaggg tcacttcgac gtatcg                                      26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
gctctagagc tcatacatca atctc                                       25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
catgccatgg tcatgtctta cc                                          22

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5
catcttcatg tcttacc                                                17

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
ggactagtga aatcaataat caacg                                       25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
```

```
gctcaacaaa gtagatcaag                                              20

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
catgccatgg ctcaacaaag tagatcaag                                    29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
ggactagttt aatgaaattg accg                                         24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
ggtactgatg tgatggctgc tatgg                                        25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
gcaacatcat cacgcagagc atc                                          23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
caacagtact gcgatgagtg g                                            21

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
gtagtgagat gaaaagag                                                18

<210> SEQ ID NO 14
<211> LENGTH: 21
<212> TYPE: DNA
<213> ORGANISM: Artificial Sequence
<220> FEATURE:
```

```
<223> OTHER INFORMATION: Description of Artificial Sequence: Primer

<400> SEQUENCE: 14
gtaggtaatg gcgttatcac g                                            21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 15
ggtggtgcgt aacggcaaag c                                            21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
cgggatccga ttcaaacaag cttg                                         24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cgggatccca tcttcatgtc tttac                                        25

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 18
aactgcagcg ctgtgacgat gctaatcc                                     28

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
aactgcagga ttcaaacaag cttg                                         24

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 20
aacaggcgcc gattcaaaca agcttg                                       26

<210> SEQ ID NO 21
```

```
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
aacaggcgcc agtatacact cc                                           22

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 22
ctatttactg attactc                                                 17

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 23
cttaatctgc tgcaatg                                                 17

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 24
ggactagtcg acgcgtttaa tgaaattgac cg                                32

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
cgacgcgtga ttcaaacaag cttg                                         24

<210> SEQ ID NO 26
<211> LENGTH: 69
<212> TYPE: PRT
<213> ORGANISM: Bacillus subtilis

<400> SEQUENCE: 26
```

Met Ala Asn Asn Asn Ser Gly Asn Ser Asn Asn Leu Leu Val Pro Gly
 1               5                  10                  15

Ala Ala Gln Ala Ile Asp Gln Met Lys Leu Glu Ile Ala Ser Glu Phe
             20                  25                  30

Gly Val Asn Leu Gly Ala Asp Thr Thr Ser Arg Ala Asn Gly Ser Val
         35                  40                  45

Gly Gly Glu Ile Thr Lys Arg Leu Val Ser Phe Ala Gln Gln Asn Met
     50                  55                  60

Gly Gly Gly Gln Phe
 65

```
<210> SEQ ID NO 27
<211> LENGTH: 67
<212> TYPE: PRT
<213> ORGANISM: Bacillus subtilis

<400> SEQUENCE: 27

Met Ala Asn Gln Asn Ser Ser Asn Asp Leu Leu Val Pro Gly Ala Ala
 1               5                  10                  15

Gln Ala Ile Asp Gln Met Lys Leu Glu Ile Ala Ser Glu Phe Gly Val
             20                  25                  30

Asn Leu Gly Ala Asp Thr Thr Ser Arg Ala Asn Gly Ser Val Gly Gly
         35                  40                  45

Glu Ile Thr Lys Arg Leu Val Ser Phe Ala Gln Gln Met Gly Gly
     50                  55                  60

Arg Val Gln
 65

<210> SEQ ID NO 28
<211> LENGTH: 72
<212> TYPE: PRT
<213> ORGANISM: Bacillus subtilis

<400> SEQUENCE: 28

Met Ala Gln Gln Ser Arg Ser Arg Ser Asn Asn Asn Asn Asp Leu Leu
 1               5                  10                  15

Ile Pro Gln Ala Ala Ser Ala Ile Glu Gln Met Lys Leu Glu Ile Ala
             20                  25                  30

Ser Glu Phe Gly Val Gln Leu Gly Ala Glu Thr Thr Ser Arg Ala Asn
         35                  40                  45

Gly Ser Val Gly Gly Glu Ile Thr Lys Arg Leu Val Arg Leu Ala Gln
     50                  55                  60

Gln Asn Met Gly Gly Gln Phe His
 65                  70

<210> SEQ ID NO 29
<211> LENGTH: 64
<212> TYPE: PRT
<213> ORGANISM: Bacillus subtilis

<400> SEQUENCE: 29

Met Ala Ser Arg Asn Lys Leu Val Val Pro Gly Val Glu Gln Ala Leu
 1               5                  10                  15

Asp Gln Phe Lys Leu Glu Val Ala Gln Glu Phe Gly Val Asn Leu Gly
             20                  25                  30

Ser Asp Thr Val Ala Arg Ala Asn Gly Ser Val Gly Gly Glu Met Thr
         35                  40                  45

Lys Arg Leu Val Gln Gln Ala Gln Ser Gln Leu Asn Gly Thr Thr Lys
     50                  55                  60

<210> SEQ ID NO 30
<211> LENGTH: 62
<212> TYPE: PRT
<213> ORGANISM: Bacillus megaterium

<400> SEQUENCE: 30

Met Ala Asn Thr Asn Lys Leu Val Ala Pro Gly Ser Ala Ala Ala Ile
 1               5                  10                  15

Asp Gln Met Lys Tyr Glu Ile Ala Ser Glu Phe Gly Val Asn Leu Gly
             20                  25                  30
```

```
Pro Glu Ala Thr Ala Arg Ala Asn Gly Ser Val Gly Gly Glu Ile Thr
            35                  40                  45

Lys Arg Leu Val Gln Met Ala Glu Gln Gln Leu Gly Gly Lys
 50                  55                  60
```

<210> SEQ ID NO 31
<211> LENGTH: 72
<212> TYPE: PRT
<213> ORGANISM: Bacillus megaterium

<400> SEQUENCE: 31

```
Met Ala Asn Tyr Gln Asn Ala Ser Asn Arg Asn Ser Ser Asn Lys Leu
 1               5                  10                  15

Val Ala Pro Gly Ala Gln Ala Ala Ile Asp Gln Met Lys Phe Glu Ile
                20                  25                  30

Ala Ser Glu Phe Gly Val Asn Leu Gly Pro Asp Ala Thr Ala Arg Ala
            35                  40                  45

Asn Gly Ser Val Gly Gly Glu Ile Thr Lys Arg Leu Val Gln Leu Ala
 50                  55                  60

Glu Gln Asn Leu Gly Gly Lys Tyr
 65                  70
```

<210> SEQ ID NO 32
<211> LENGTH: 69
<212> TYPE: PRT
<213> ORGANISM: Bacillus megaterium

<400> SEQUENCE: 32

```
Met Ala Asn Asn Asn Ser Ser Asn Asn Asn Glu Leu Leu Val Tyr Gly
 1               5                  10                  15

Ala Glu Gln Ala Ile Asp Gln Met Lys Tyr Glu Ile Ala Ser Glu Phe
                20                  25                  30

Gly Val Asn Leu Gly Ala Asp Thr Thr Ala Arg Ala Asn Gly Ser Val
            35                  40                  45

Gly Gly Glu Ile Thr Lys Arg Leu Val Gln Leu Ala Glu Gln Gln Leu
 50                  55                  60

Gly Gly Gly Arg Phe
 65
```

<210> SEQ ID NO 33
<211> LENGTH: 73
<212> TYPE: PRT
<213> ORGANISM: Bacillus megaterium

<400> SEQUENCE: 33

```
Met Ala Asn Asn Lys Ser Ser Asn Asn Asn Glu Leu Leu Val Tyr Gly
 1               5                  10                  15

Ala Glu Gln Ala Ile Asp Gln Met Lys Tyr Glu Ile Ala Ser Glu Phe
                20                  25                  30

Gly Val Asn Leu Gly Ala Asp Thr Thr Ala Arg Ala Asn Gly Ser Val
            35                  40                  45

Gly Gly Glu Ile Thr Lys Arg Leu Val Gln Leu Ala Glu Gln Gln Leu
 50                  55                  60

Gly Gly Gly Arg Ser Lys Thr Thr Leu
 65                  70
```

<210> SEQ ID NO 34
<211> LENGTH: 65
<212> TYPE: PRT

<213> ORGANISM: Bacillus megaterium

<400> SEQUENCE: 34

Met Ala Arg Thr Asn Lys Leu Leu Thr Pro Gly Val Glu Gln Phe Leu
1               5                   10                  15

Asp Gln Tyr Lys Tyr Glu Ile Ala Gln Glu Phe Gly Val Thr Leu Gly
            20                  25                  30

Ser Asp Thr Ala Ala Arg Ser Asn Gly Ser Val Gly Gly Glu Ile Thr
        35                  40                  45

Lys Arg Leu Val Gln Gln Ala Gln Ala His Leu Ser Gly Ser Thr Gln
    50                  55                  60

Lys
65

<210> SEQ ID NO 35
<211> LENGTH: 69
<212> TYPE: PRT
<213> ORGANISM: Bacillus megaterium

<400> SEQUENCE: 35

Met Ala Asn Asn Lys Ser Ser Asn Asn Glu Leu Leu Val Tyr Gly
1               5                   10                  15

Ala Glu Gln Ala Ile Asp Gln Met Lys Tyr Glu Ile Ala Ser Glu Phe
            20                  25                  30

Gly Val Asn Leu Gly Ala Asp Thr Thr Ala Arg Ala Asn Gly Ser Val
        35                  40                  45

Gly Gly Glu Ile Thr Lys Arg Leu Val Gln Leu Ala Glu Gln Gln Leu
    50                  55                  60

Gly Gly Gly Arg Phe
65

<210> SEQ ID NO 36
<211> LENGTH: 73
<212> TYPE: PRT
<213> ORGANISM: Bacillus megaterium

<400> SEQUENCE: 36

Met Ala Asn Ser Arg Asn Lys Ser Ser Asn Glu Leu Ala Val His Gly
1               5                   10                  15

Ala Gln Gln Ala Ile Asp Gln Met Lys Tyr Glu Ile Ala Ser Glu Phe
            20                  25                  30

Gly Val Thr Leu Gly Pro Asp Thr Thr Ala Arg Ala Asn Gly Ser Val
        35                  40                  45

Gly Gly Glu Ile Thr Lys Arg Leu Val Gln Met Ala Glu Gln Gln Leu
    50                  55                  60

Gly Gly Gly Arg Ser Lys Ser Leu Ser
65                  70

<210> SEQ ID NO 37
<211> LENGTH: 68
<212> TYPE: PRT
<213> ORGANISM: Bacillus megaterium

<400> SEQUENCE: 37

Met Ala Asn Asn Asn Ser Ser Asn Asn Glu Leu Leu Val Tyr Gly
1               5                   10                  15

Ala Glu Gln Ala Ile Asp Gln Met Lys Tyr Glu Ile Ala Ser Glu Phe
            20                  25                  30

Gly Val Asn Leu Gly Ala Asp Thr Thr Ala Arg Ala Asn Gly Ser Val

```
                    35                  40                  45
Gly Gly Glu Ile Thr Lys Arg Leu Val Gln Leu Ala Glu Gln Leu Gly
        50                  55                  60

Gly Gly Arg Phe
 65

<210> SEQ ID NO 38
<211> LENGTH: 72
<212> TYPE: PRT
<213> ORGANISM: Bacillus megaterium

<400> SEQUENCE: 38

Met Ala Asn Asn Lys Ser Ser Asn Asn Glu Leu Leu Val Tyr Gly
 1               5                  10                  15

Ala Glu Gln Ala Ile Asp Gln Met Lys Tyr Glu Ile Ala Ser Glu Phe
            20                  25                  30

Gly Val Asn Leu Gly Ala Asp Thr Thr Ala Arg Ala Asn Gly Ser Val
        35                  40                  45

Gly Gly Glu Ile Thr Lys Arg Leu Val Gln Leu Ala Glu Gln Leu Gly
    50                  55                  60

Gly Gly Arg Ser Lys Thr Thr Leu
 65                  70

<210> SEQ ID NO 39
<211> LENGTH: 70
<212> TYPE: PRT
<213> ORGANISM: Bacillus cereus

<400> SEQUENCE: 39

Met Gly Lys Asn Asn Ser Gly Ser Arg Asn Glu Val Leu Val Arg Gly
 1               5                  10                  15

Ala Glu Gln Ala Leu Asp Gln Met Lys Tyr Glu Ile Ala Gln Glu Phe
            20                  25                  30

Gly Val Gln Leu Gly Ala Asp Thr Thr Ala Arg Ser Asn Gly Ser Val
        35                  40                  45

Gly Gly Glu Ile Thr Lys Arg Leu Val Ala Met Ala Glu Gln Gln Leu
    50                  55                  60

Gly Gly Arg Ala Asn Arg
 65                  70

<210> SEQ ID NO 40
<211> LENGTH: 65
<212> TYPE: PRT
<213> ORGANISM: Bacillus cereus

<400> SEQUENCE: 40

Met Ser Arg Ser Thr Asn Lys Leu Ala Val Pro Gly Ala Glu Ser Ala
 1               5                  10                  15

Leu Asp Gln Met Lys Tyr Glu Ile Ala Gln Glu Phe Gly Val Gln Leu
            20                  25                  30

Gly Ala Asp Ala Thr Ala Arg Ala Asn Gly Ser Val Gly Gly Glu Ile
        35                  40                  45

Thr Lys Arg Leu Val Ser Leu Ala Glu Gln Gln Leu Gly Gly Tyr Gln
    50                  55                  60

Lys
 65

<210> SEQ ID NO 41
<211> LENGTH: 76
```

<212> TYPE: PRT
<213> ORGANISM: Bacillus cereus

<400> SEQUENCE: 41

```
Met Leu Phe Ile Asn Ile Gln Arg Tyr Glu Ser Asp Thr Asn Glu Ile
  1               5                  10                  15

Leu Ile Ser Ala Thr Thr Ser Thr Ile Glu Gln Met Lys Tyr Glu Ile
             20                  25                  30

Ala Phe Glu Leu Gly Val Thr Leu Gly Pro Asp Thr Ser His His Leu
         35                  40                  45

Gln Met Val Arg Ile Gly Gly Glu Ile Thr Lys Arg Leu Val Arg Met
     50                  55                  60

Ala Glu Lys Gln Leu Thr Gly Gln Tyr Arg Leu His
 65                  70                  75
```

<210> SEQ ID NO 42
<211> LENGTH: 70
<212> TYPE: PRT
<213> ORGANISM: Bacillus stearothermophilus

<400> SEQUENCE: 42

```
Met Pro Asn Gln Ser Gly Ser Asn Ser Ser Asn Gln Leu Leu Val Pro
  1               5                  10                  15

Gly Ala Ala Gln Val Ile Asp Gln Met Lys Phe Glu Ile Ala Ser Glu
             20                  25                  30

Phe Gly Val Asn Leu Gly Ala Glu Thr Thr Ser Arg Ala Asn Gly Ser
         35                  40                  45

Val Gly Gly Glu Ile Thr Lys Arg Leu Val Ser Phe Ala Gln Gln Gln
     50                  55                  60

Met Gly Gly Gly Val Gln
 65                  70
```

<210> SEQ ID NO 43
<211> LENGTH: 67
<212> TYPE: PRT
<213> ORGANISM: Bacillus thermus

<400> SEQUENCE: 43

```
Met Ala Asn Asn Asn Ser Ser Asn Gln Leu Val Val Pro Gly Val Gln
  1               5                  10                  15

Gln Ala Leu Asp Gln Met Lys Tyr Glu Ile Ala Ser Glu Phe Gly Val
             20                  25                  30

Gln Leu Gly Pro Asp Ala Thr Ala Arg Ala Asn Gly Ser Val Gly Gly
         35                  40                  45

Glu Ile Thr Lys Arg Leu Val Gln Met Ala Glu Gln Gln Met Gly Gly
     50                  55                  60

Tyr Gln Lys
 65
```

<210> SEQ ID NO 44
<211> LENGTH: 70
<212> TYPE: PRT
<213> ORGANISM: Clostridium bifermentans

<400> SEQUENCE: 44

```
Thr Thr Asn Asn Asn Asn Thr Lys Ala Val Pro Glu Ala Lys Ala Ala
  1               5                  10                  15

Leu Lys Gln Met Lys Leu Glu Ile Ala Asn Glu Leu Gly Ile Ser Asn
             20                  25                  30
```

Tyr Asp Thr Ala Asp Lys Gly Asn Met Thr Ala Arg Gln Asn Gly Tyr
            35                  40                  45

Val Gly Gly Tyr Met Thr Lys Lys Leu Val Glu Met Ala Glu Gln Gln
 50                  55                  60

Met Ser Gly Gln Gln Arg
 65                  70

<210> SEQ ID NO 45
<211> LENGTH: 64
<212> TYPE: PRT
<213> ORGANISM: Clostridium bifermentans

<400> SEQUENCE: 45

Ser Thr Lys Lys Ala Val Pro Glu Ala Lys Ala Leu Asn Gln Met
 1               5                  10                  15

Lys Leu Glu Ile Ala Asn Glu Leu Gly Leu Ser Asn Tyr Glu Ser Val
                20                  25                  30

Asp Lys Gly Asn Leu Thr Ala Arg Gln Asn Gly Tyr Val Gly Gly Tyr
            35                  40                  45

Met Thr Lys Lys Leu Val Glu Met Ala Glu Arg Gln Met Ser Gly Lys
 50                  55                  60

<210> SEQ ID NO 46
<211> LENGTH: 60
<212> TYPE: PRT
<213> ORGANISM: Clostridium perfringens

<400> SEQUENCE: 46

Met Ser Lys Ser Leu Val Pro Glu Ala Lys Asn Gly Leu Ser Lys Phe
 1               5                  10                  15

Lys Asn Glu Val Ala Arg Glu Leu Gly Val Pro Phe Ser Asp Tyr Asn
                20                  25                  30

Gly Asp Leu Ser Ser Arg Gln Cys Gly Ser Val Gly Gly Glu Met Val
            35                  40                  45

Lys Arg Met Val Glu Ala Tyr Glu Ser Gln Ile Lys
 50                  55                  60

<210> SEQ ID NO 47
<211> LENGTH: 59
<212> TYPE: PRT
<213> ORGANISM: Clostridium perfringens

<400> SEQUENCE: 47

Met Ser Gln His Leu Val Pro Glu Ala Lys Asn Gly Leu Ser Lys Phe
 1               5                  10                  15

Lys Asn Glu Val Ala Ala Glu Met Gly Val Pro Phe Ser Asp Tyr Asn
                20                  25                  30

Gly Asp Leu Ser Ser Lys Gln Cys Gly Ser Val Gly Gly Glu Met Val
            35                  40                  45

Lys Arg Met Val Glu Gln Tyr Glu Lys Gly Ile
 50                  55

<210> SEQ ID NO 48
<211> LENGTH: 60
<212> TYPE: PRT
<213> ORGANISM: Clostridium perfringens

<400> SEQUENCE: 48

Met Ser Gln His Leu Val Pro Glu Ala Lys Asn Gly Leu Ser Lys Phe
 1               5                  10                  15

```
Lys Asn Glu Val Ala Asn Glu Met Gly Val Pro Phe Ser Asp Tyr Asn
                20                  25                  30

Gly Asp Leu Ser Ser Arg Gln Cys Gly Ser Val Gly Gly Glu Met Val
            35                  40                  45

Lys Arg Met Val Glu Lys Tyr Glu Gln Ser Met Lys
        50                  55                  60

<210> SEQ ID NO 49
<211> LENGTH: 72
<212> TYPE: PRT
<213> ORGANISM: Sporosarcina halophila

<400> SEQUENCE: 49

Met Ala Asn Asn Ser Ser Asn Glu Leu Val Val Pro Gly Val Gln
1               5                   10                  15

Gln Ala Leu Asp Gln Met Lys Tyr Glu Ile Ala Gln Glu Phe Gly Val
            20                  25                  30

Gln Leu Gly Ala Asp Ser Thr Ser Arg Ala Asn Gly Ser Val Gly Gly
        35                  40                  45

Glu Ile Thr Lys Arg Leu Val Gln Met Ala Glu Gln Phe Gly Gly
    50                  55                  60

Gln Gln Tyr Gly Gln Gln Gln Lys
65                  70

<210> SEQ ID NO 50
<211> LENGTH: 69
<212> TYPE: PRT
<213> ORGANISM: Sporosarcina ureae

<400> SEQUENCE: 50

Met Thr Asn Asn Asn Ser Asn Ser Asn Gln Leu Leu Val Pro Gly
1               5                   10                  15

Val Gln Gln Ala Ile Asn Gln Met Lys Glu Glu Ile Ala Asn Glu Phe
            20                  25                  30

Gly Val Asn Leu Gly Pro Asp Ser Thr Ser Arg Ala Asn Gly Ser Val
        35                  40                  45

Gly Gly Glu Ile Thr Lys Arg Leu Val Arg Gln Ala Gln Ser Gln Met
    50                  55                  60

Asn Gly Tyr Thr Lys
65

<210> SEQ ID NO 51
<211> LENGTH: 67
<212> TYPE: PRT
<213> ORGANISM: Sporosarcina ureae

<400> SEQUENCE: 51

Met Pro Asn Asn Ser Ser Asn Gln Leu Leu Val Pro Gly Val Gln
1               5                   10                  15

Gln Ala Leu Asn Gln Met Lys Glu Glu Ile Ala Ser Glu Phe Gly Val
            20                  25                  30

Gln Leu Gly Pro Asp Ala Ser Arg Ala Asn Gly Ser Val Gly Gly
        35                  40                  45

Glu Ile Thr Lys Arg Leu Val Arg Gln Ala Gln Ser Gln Met Asn Gly
    50                  55                  60

Tyr Thr Lys
65

<210> SEQ ID NO 52
```

```
<211> LENGTH: 71
<212> TYPE: PRT
<213> ORGANISM: Thermoactinomyces thalpophilus

<400> SEQUENCE: 52

Met Ala Gln Gln Gly Arg Asn Arg Ser Ser Asn Gln Leu Leu Val Ala
 1               5                  10                  15

Gly Ala Ala Gln Ala Ile Asp Gln Met Lys Phe Glu Ile Ala Gln Glu
             20                  25                  30

Phe Gly Val Thr Leu Gly Ala Asp Thr Thr Ser Arg Ala Asn Gly Ser
         35                  40                  45

Val Gly Gly Glu Ile Thr Lys Arg Leu Val Ser Leu Ala Gln Gln Gln
     50                  55                  60

Leu Gly Gly Gly Thr Ser Phe
 65                  70

<210> SEQ ID NO 53
<211> LENGTH: 272
<212> TYPE: DNA
<213> ORGANISM: Bacillus subtilis

<400> SEQUENCE: 53
atggctcaac aaagtagatc aagatcaaac aacaataatg atttactaat tcctcaagca      60
gcttcagcta ttgaacaaat gaaacttgaa atagcttctg agtttggtgt tcaattaggc     120
gctgagacta catctcgtgc aaacggttca gttggtggag aaatcactaa acgtttagtt     180
cgcttagctc aacaaaacat gggcggtcaa tttcattaat ttatgagggg gataattccc     240
ctctcttttt taagtcttct ctaaatccat ac                                   272

<210> SEQ ID NO 54
<211> LENGTH: 823
<212> TYPE: DNA
<213> ORGANISM: Bacteriophage lambda

<400> SEQUENCE: 54
ctagttggtc acttcgacgt atcgtctgga actccaacca tcgcaggcag agaggtctgc      60
aaaatgcaat cccgaaacag ttcgcaggta atagttagag cctgcataac ggtttcggga     120
ttttttatat ctgcacaaca ggtaagagca ttgagtcgat aatcgtgaag agtcggcgag     180
cctggttagc cagtgctctt tccgttgtgc tgaattaagc gaataccgga agcagaaccg     240
gatcaccaaa tgcgtacagg cgtcatcgcc gcccagcaac agcacaaccc aaactgagcc     300
gtagccactg tctgtcctga attcattagt aatagttacg ctgcggcctt ttacacatga     360
ccttcgtgaa agcgggtggc aggaggtcgc gctaacaacc tcctgccgtt ttgcccgtgc     420
atatcggtca cgaacaaatc tgattactaa acacagtagc ctggatttgt tctatcagta     480
atcgacctta ttcctaatta aatagagcaa atcccttat tggggtaag acatgaccat     540 ggctcaacaa agtagatcaa gatcaaacaa caataatgat ttactaattc ctcaagcagc     600
ttcagctatt gaacaaatga aacttgaaat agcttctgag tttggtgttc aattaggcgc     660
tgagactaca tctcgtgcaa acggttcagt tggtggagaa atcactaaac gtttagttcg     720
cttagctcaa caaacatgg gcggtcaatt tcattaaact agtgcaccaa taactgcctt     780
aaaaaaatta cgccccgccc tgccactcat cgcagtactg ttg                       823

<210> SEQ ID NO 55
<211> LENGTH: 566
<212> TYPE: DNA
<213> ORGANISM: Bacteriophage lambda
```

```
<400> SEQUENCE: 55
tgttcagcta ctgacggggt ggtgcgtaac ggcaaaagca ccgccggaca tcagcgctag      60
cggagtgtat actggactag tgaaatcaat aatcaacgta aggcgttcct cgatatgctg     120
gcgtggtcgg agggaactga taacggacgt cagaaaacca gaaatcatgg ttatgacgtc     180
attgtaggcg gagagctatt tactgattac tccgatcacc ctcgcaaact tgtcacgcta     240
aacccaaaac tcaaatcaac aggcgccgga cgctaccagc ttcttcccg ttggtgggat      300 gcctaccgca agcagcttgg cctgaaagac ttctctccga aaagtcagga cgctgtggca     360
ttgcagcaga ttaaggagcg tggcgcttta cctatgattg atcgtggtga tatccgtcag     420
gcaatcgacc gttgcagcaa tatctgggct tcactgccgg cgctggtta tggtcagttc      480 gagcataagg ctgacagcct gattgcaaaa ttcaaagaag cgggcggaac ggtcagagag     540
attgatgtat gagcagagtc accgcg                                          566

<210> SEQ ID NO 56
<211> LENGTH: 402
<212> TYPE: DNA
<213> ORGANISM: Bacteriophage lambda

<400> SEQUENCE: 56
ctcgatcccg cgaaattaat acgactcact atagggaat tgtgagcgga taacaattcc      60
cctctagaaa taattttgtt aactttaag aaggagatat accatggctc aacaaagtag     120
atcaagatca acaacaata atgatttact aattcctcaa gcagcttcag ctattgaaca     180
aatgaaactt gaaatagctt ctgagtttgg tgttcaatta ggcgctgaga ctacatctcg     240
tgcaaacggt tcagttggtg gagaaatcac taaacgttta gttcgcttag ctcaacaaaa     300
catgggcggt caatttcatt aatttatgag ggggataatt cccctctctt ttttaagtct    360
tctctaaatc catacctcga gcaccaccac caccaccact ga                       402

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtaagacat gaagatgcca gaa                                             23

<210> SEQ ID NO 58
<211> LENGTH: 30
<212> TYPE: DNA
<213> ORGANISM: Bacillus subtilis

<400> SEQUENCE: 58
atggctcaac aaagtagatc aagatcaaac                                      30

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggtaagacat gaagatggct caacaaagta gatcaag                              37
```

```
<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggtaagacat gaccatggct caacaaagta gatcaag                              37
```